United States Patent [19]
Klump et al.

[11] Patent Number: 5,698,446
[45] Date of Patent: Dec. 16, 1997

[54] METHODS AND COMPOSITIONS FOR INHIBITING PRODUCTION OF REPLICATION COMPETENT VIRUS

[75] Inventors: Wolfgang M. Klump, Del Mar; Douglas J. Jolly, Leucadia, both of Calif.

[73] Assignee: Chiron Corporation

[21] Appl. No.: 305,699

[22] Filed: Sep. 7, 1994

[51] Int. Cl.$^6$ .................. C12N 5/10; C12N 15/86
[52] U.S. Cl. .................. 435/350; 435/320.1; 435/366
[58] Field of Search .................. 435/69.1, 172.1, 435/172.3, 240.2, 320.1, 325, 350, 352, 366; 536/23.1, 23.7, 24.1

[56] References Cited

FOREIGN PATENT DOCUMENTS

| WO/8907150 | 8/1989 | WIPO . |
| WO 91/02805 | 3/1991 | WIPO . |
| WO 92/05266 | 4/1992 | WIPO . |
| WO 95/30763 | 11/1995 | WIPO . |

OTHER PUBLICATIONS

Harrison et al, "Inhibition of Human Immunodeficiency Virus-1 Production Resulting from Transduction with a Retrovirus Containing an HIV-Regulated Diphtheria Toxin A chain Gene", Human Gene Theory, vol. 3, 1992, pp. 461–469.

Bacchetti and Graham, Proc. Natl. Acad. Sci. 74(4):1590–1594, 1977.
Borrelli et al., Proc. Natl. Acad. Sci. 85:7572–7576, 1988.
Bosselman, Molec. and Cell. Biol. 1797–1806.
Danos and Mulligan, Proc. Natl. Acad. Sci. 85:6460–6464, 1988.
Fisher, et al., Infection and Immunity 3562–3565, 1991.
Haseloff and Gerlach, Nature 334:585–591, 1988.
Lawn et al., Cell 21:647–651, 1980.
Markowitz et al., Annals NY Acad. Sci. 407–414.
Markowitz et al., Virology 167:400–406, 1988.
Maxwell et al., Cancer Research 46:4660–4664, 1986.
Ormondt et al., Gene 11:299–309, 1980.
Peace et al., J. Exp. Med. 179:473–479, 1994.
Wagner et al., Proc. Natl. Acad. Sci. 78(3):1441–1445, 1981.
Wilk et al., Nucl. Acids Research 18(8):2065–2068, 1990.

*Primary Examiner*—David Guzo
*Attorney, Agent, or Firm*—Norman J. Kruse; Robert P. Blackburn

[57] ABSTRACT

The present invention provides methods and compositions for inhibiting the production of replication competent virus. The invention comprises nucleic acid cassettes encoding a non-biologically active inhibitory molecule which are incorporated into packaging cells and recombinant vector constructs. Upon recombination between various vector construct contained within the producer cell, a biologically active molecule is produced which kills the cell, thereby inhibiting production of replication competent virus.

25 Claims, 10 Drawing Sheets

METHODS AND COMPOSITIONS FOR INHIBITING PRODUCTION OF REPLICATION COMPETENT VIRUS

TECHNICAL FIELD

The present invention relates generally to the field of viral-mediated gene transfer and, more specifically, to compositions and methods for preventing the production of replication competent virus resulting from recombination events in packaging cells.

BACKGROUND OF THE INVENTION

The introduction of normal genes into the dividing cells of individuals to treat disease on the genetic level is termed gene therapy and has been the focus of much research over the past decade. At present, retroviruses are the vehicles frequently chosen to deliver exogenous genes into human cells. This is primarily due to the high efficiency of retroviral gene transfer, as well as the fact that the retroviral proteins necessary to form the virion particle can be supplied in trans. A retroviral gene transfer system generally employs a retroviral vector containing the gene of interest to be transferred, and a helper or "packaging" cell which provides gag, pol and env proteins required to produce the viral particle. The retroviral vector typically contains flanking viral long terminal repeats (LTRs) and a packaging sequence (Ψ) but lacks the gag, pol and env gene sequences. The helper virus, contained in a packaging cell line, has a deletion of the Ψ packaging sequence, which is required in cis for the packaging of retroviral RNA into the virion (see FIG. 1). The deletion inactivates the packaging signal and the helper virus becomes replication defective.

An important prerequisite for the use of retroviruses in gene therapy is the availability of retroviral packaging cell lines incapable of producing replication competent, or "wild-type," virus. The proliferation of wild-type virus may lead to multiple integrations into the genome of a patient's cell(s) which may result in the activation of potentially harmful genes such as oncogenes. One possibility in the use of retroviral vectors is that replication-competent retroviruses could be generated through events in which an intact Ψ sequence from a retroviral vector is recombined to correct the deleted Ψ sequence of the helper virus. Packaging cell lines wherein the helper viral genome contains additional mutations, including deletions of the 3' LTR and portions of the 5' LTR, have been constructed as improved alternatives to previously used cell lines to prevent production of replication-competent viral particles. For instance, when the cell line PA317 is used, two recombination events are necessary to form a replication competent genome. PA317 is an amphotropic packaging cell line in which there is a deletion of the Ψ sequence and where env and gag/pol are present on a single genome. Nevertheless, replication competent virus can still be generated using PA317 cells even when several mutations are present.

Another approach has been to separate the viral gag, pol, and env genes of the helper virus onto two plasmids with gag and pol on one plasmid and env on the other (Markowitz et al., *Vir.* 167:400, 1988). In addition, the Ψ packaging sequence and the 3' LTR were removed in both plasmids. When these packaging lines are used, at least three recombination events between the helper virus genome and the retroviral vector are necessary to generate a replication competent virus. The efficiency of gene transfer using this approach was comparable to that of packaging lines containing the helper virus genes on one plasmid. However, despite this approach, generation of replication-competent virus has been detected with these packaging cell lines (Markowitz et al., *Ann. N.Y. Acad. Sci.* 612:407, 1990).

In addition to retroviral vectors, the importance of packaging systems for other vectors such as adenoviral vectors, herpes viral vectors, Sindbis viral vectors, and adeno-associated viral vectors is becoming apparent. All viral vectors are preferably non-replicating (i.e., defective) and preferably carry no or few viral protein coding regions that may cause toxicity in target cells or elicit unwanted immune responses. For most, if not all viral vector systems, it is important to have packaging cells, and that these cells do not lead to partial or total reconstruction of a replicating virus. Consequently, there is a need in the field of gene therapy for a system that will be even more effective in preventing the generation of replication competent virus.

SUMMARY OF THE INVENTION

It is the object of the present invention to provide vectors that inhibit the production of replication competent virus resulting from recombination events in packaging and producer cells. Within one aspect of the present invention, a vector is provided for directing the expression of a viral structural polypeptide, the vector comprising a promoter operably associated with a structural gene construct and a polyadenylation signal, the structural gene construct comprising a nucleic acid molecule coding for a viral structural polypeptide and a non-biologically active inhibitory molecule.

In one embodiment of this aspect, the viral structural polypeptide encoded by the structural gene construct is selected from a retroviral env and gag/pol gene product. In particular, env is encoded by an env gene derived from a viral genome isolated from one of the following retroviruses: Murine leukemia virus (MLV); (e.g., Moloney MLV strain 4070A); human T-cell leukemia virus-I (HTLV-I, HTLV-II); human immunodeficiency virus (HIV), Mason Pfizer monkey virus (MPMV) or other simian D type viruses, such as SRV-I, human or monkey foamyvirus (HFV or MFV), Simian immunodeficiency virus (SIV), gibbon ape leukemia virus (GALV), bovine leukemia virus (BLV); feline leukemia virus (FeLV); and feline immunodeficiency virus (FIV). In addition, the env gene may be selected from amphotropic, polytropic, xenotropic or ecotropic retrovirus strains or mutants thereof. Within preferred embodiments of the invention, the env gene is derived from a murine amphotropic retrovirus and gag/pol gene is derived from a MoMLV retrovirus.

Within another embodiment of this aspect of the invention, the promoter is selected from the group consisting of rous sarcoma virus (RSV), adenovirus major late promoter (MLP), simian virus 40 (SV40) and cytomegalovirus major immediate early promoter (CMV MIE). Within a preferred embodiment, the promoter is CMV MIE.

Within yet another embodiment of this aspect of the invention, the non-biologically active inhibitory molecule encoded by the structural gene construct is a toxin, a ribozyme, or a prodrug activating enzyme. When a gene encoding a toxin is employed, the toxin is preferably selected from the group consisting of tetanus, ricin A chain, and in particular, diphtheria toxin. Should a ribozyme be employed, it will have an active site that binds and cleaves the mRNA transcript of the replication competent retrovirus resulting from a recombination event in the packaging (or producer) cell. A prodrug activating enzyme, such as herpes simplex thymidine kinase (HSVTK) may also be employed, where cells expressing active HSVTK can be eliminated by cultivation in the presence of drugs such as gancyclovir, acyclovir, FIAU or FIAC etc.

Within a particularly preferred embodiment of this aspect of the invention, the vector for directing the expression of a viral structural polypeptide comprises a CMV MIE promoter operably associated with a nucleic acid molecule encoding a gag/pol polypeptide, or a murine amphotropic env polypeptide and a non-biologically active inhibitory molecule.

Within another aspect of the invention, a vector is provided for directing the expression of a viral structural polypeptide comprising a promoter operably associated with a structural gene construct and polyadenylation signal, the structural gene construct comprising a nucleic acid molecule coding for the viral structural polypeptide, a non-biologically active inhibitory molecule and a splice site adjacent to the nucleic acid molecule coding for the non-biologically active inhibitory molecule. In one embodiment of this aspect of the invention, the splice site is derived from SV40 and β-globin, with a splice site from the β-globin gene being particularly preferred.

Within a further aspect of the invention, a recombinant vector is provided comprising an LTR, a packaging signal, a gene of interest, and a nucleic acid cassette comprising a nucleic acid molecule encoding a non-biologically active inhibitory molecule which, upon recombination with a vector described above, results in a nucleic acid molecule encoding a biologically active inhibitory molecule. In one embodiment of this aspect of the invention, the recombinant vector further comprises a selectable marker. The selectable marker may be selected from the group consisting of hygromycin, ampicillin, kanamycin, and neomycin, among others. One particularly preferred selectable marker is neomycin. In another embodiment of the invention, the nucleic acid molecule encoding a biologically active inhibitory acid molecule is contained in an LTR. In a further embodiment, the recombinant vector is a retroviral vector.

In yet another aspect of the invention, a packaging cell is provided comprising one vector encoding a gag/pol polypeptide and another vector encoding an env polypeptide from any of the above described vectors. A preferred packaging cell comprises a vector encoding a gag/pol polypeptide derived from a MoMLV retrovirus and a vector encoding an env polypeptide derived from a retrovirus selected from MoMLV, 4070A, HTLV-I, HTLV-II, HIV, MPMV, SRV-I, HFV, MFV, SIV, GALV, BLV, FeLV, and FIV. Also preferred is a packaging cell comprising a vector having a CMV MIE promoter operably associated with a nucleic acid molecule encoding a gag/pol polypeptide, a murine amphotropic env polypeptide, and a non-biologically active inhibitory molecule. In one embodiment of this aspect of the invention, the packaging cell is Ψ2, HT1080, 293, or D17, the preferred cell.

Within another aspect of the invention a producer cell is provided comprising a packaging cell transduced with a recombinant vector according to the invention. Within still another aspect of the invention are viral particles produced by such producer cells, as well as a target cell transformed with these viral particles. A preferred target cell is an animal cell, in particular a human cell.

DEFINITION OF TERMS

Figure 1:
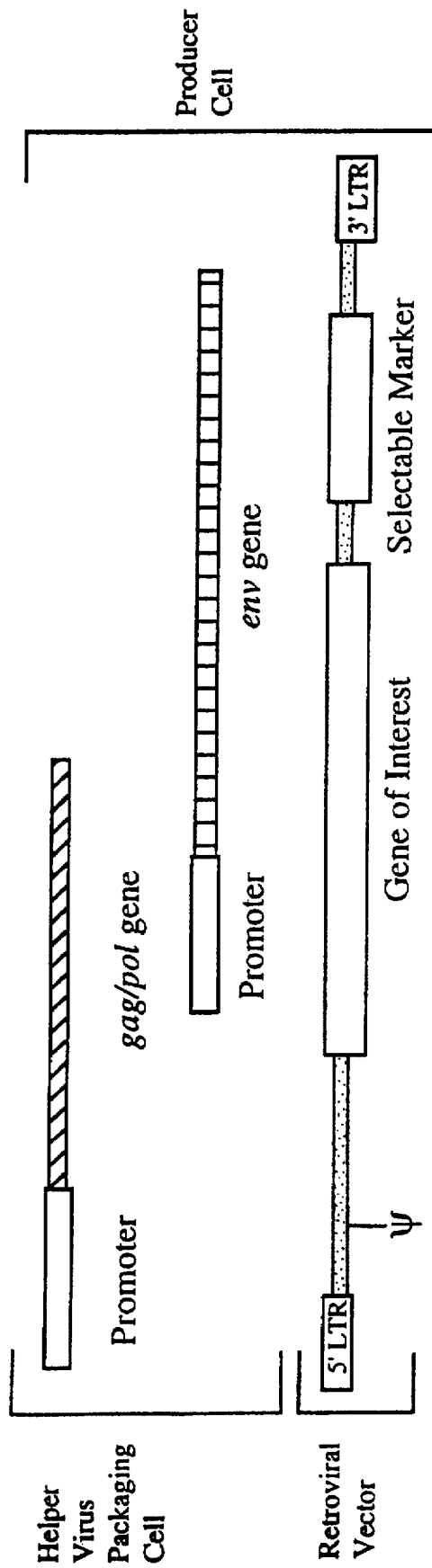
FIG. 1 is a schematic illustration of a retroviral gene transfer system employing two vectors expressing packaging protein and a retroviral vector. The packaging cell contains only the helper viral genomes, one encoding gag/pol, the other encoding env. Neither helper genomes includes a Ψ sequence. This figure further depicted a producer cell which, in addition to the helper genomes, also comprises a Ψ-carrying retroviral vector comprising the gene of interest, a selectable marker and 5' and 3' LTRs.
Figure 2A:
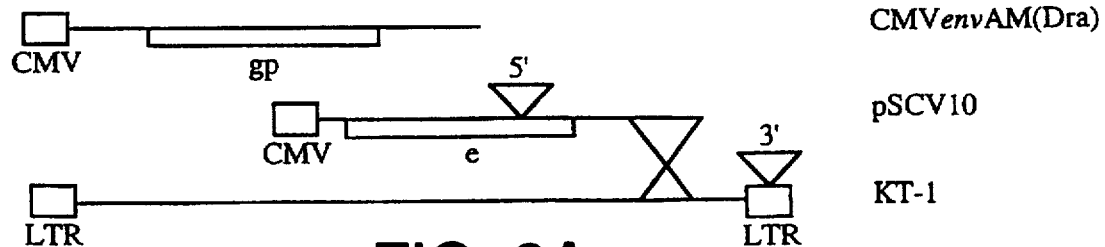
FIGS. 2a–j are schematic illustrations of proposed genomes and recombinant viral vectors comprising nucleic acid cassettes in a variety of combinations within packaging or producer cells.
Figure 2B:
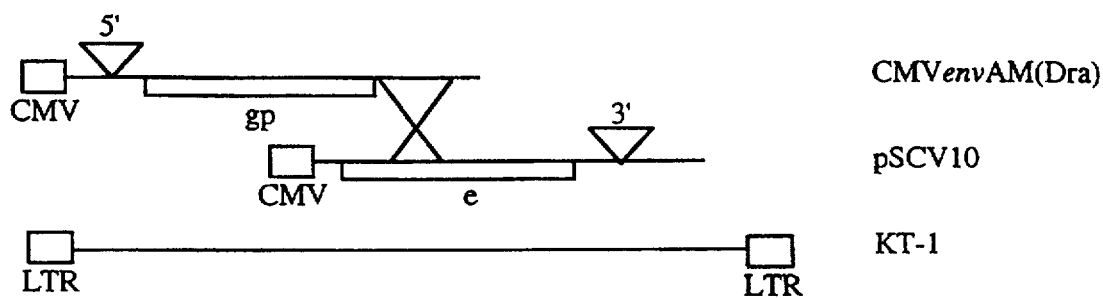
Figure 2C:
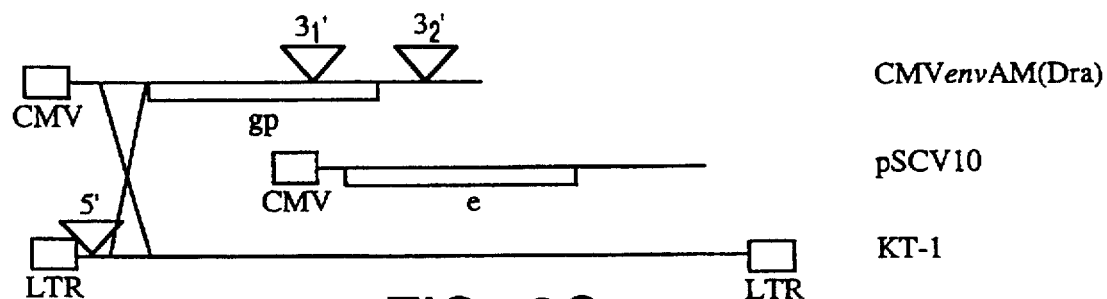
Figure 2D:
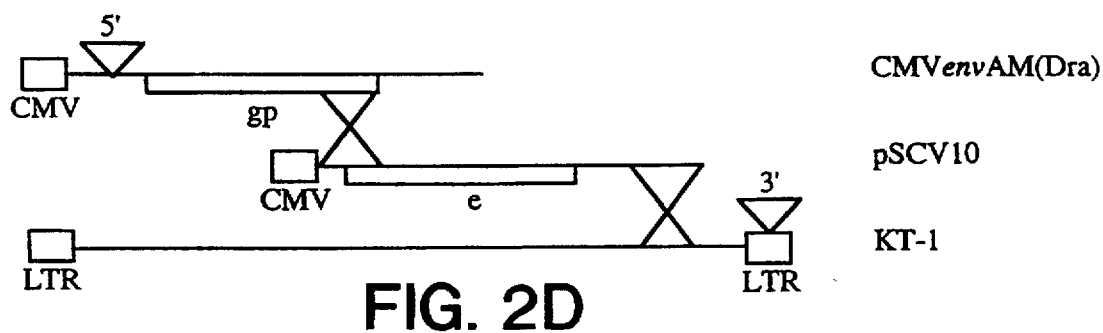
Figure 2E:
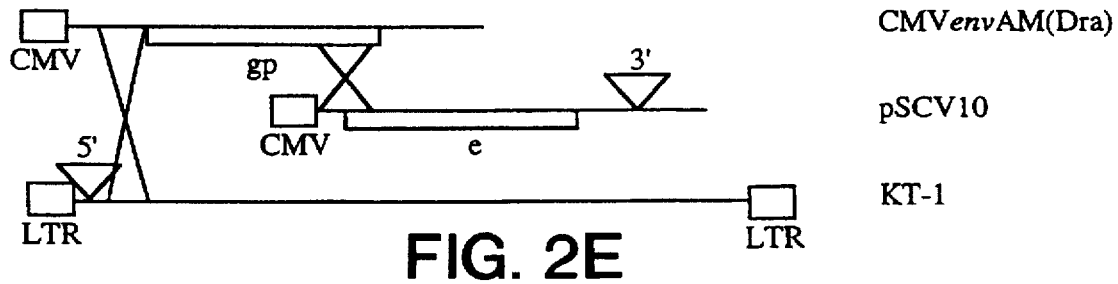
Figure 2F:
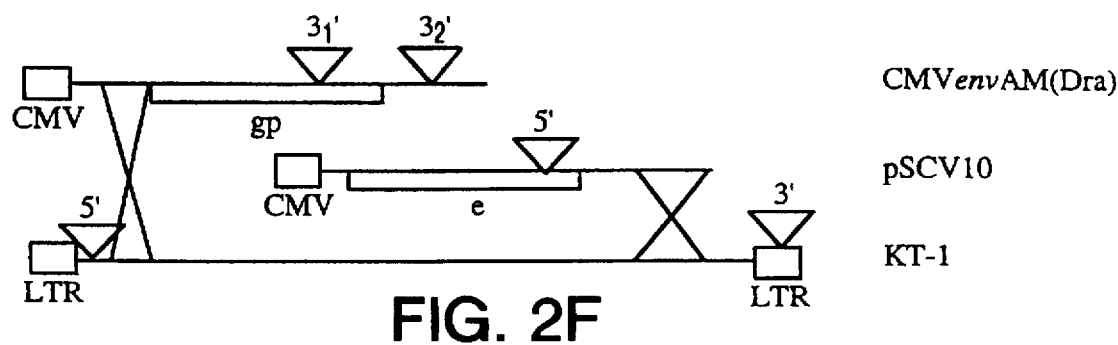
Figure 2G:
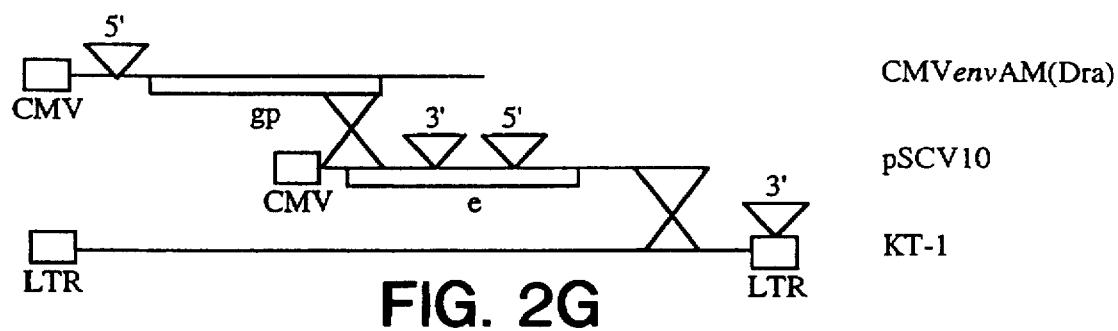
Figure 2H:
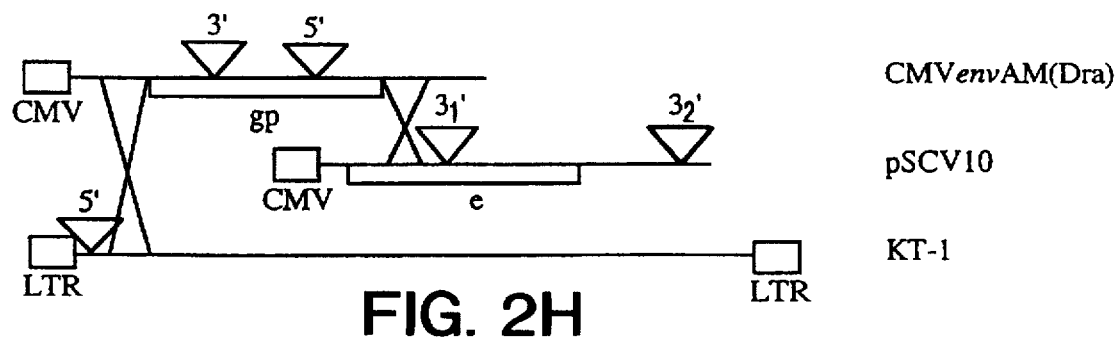
Figure 2I:
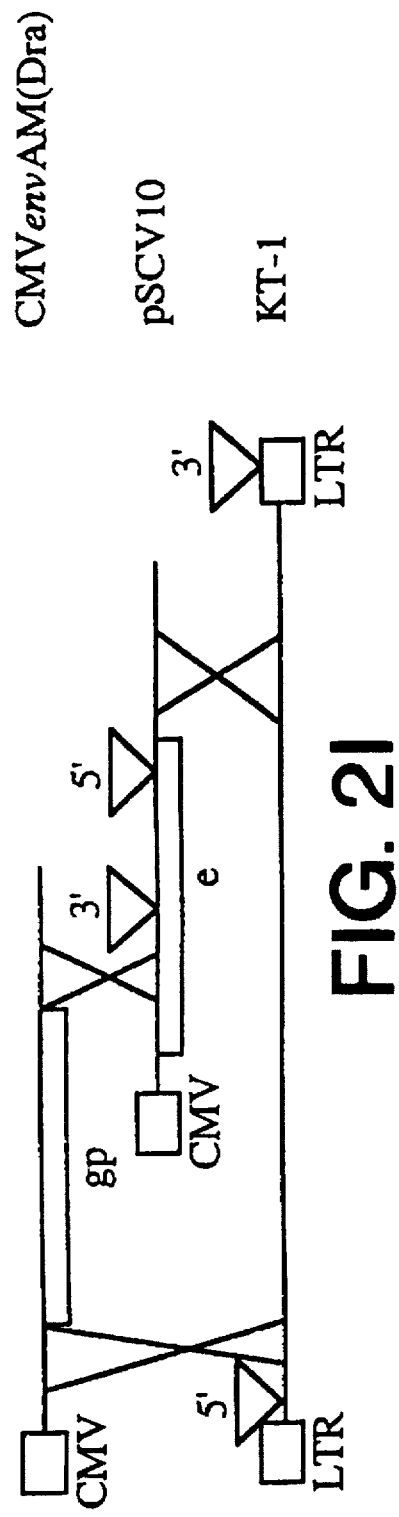
Figure 2J:
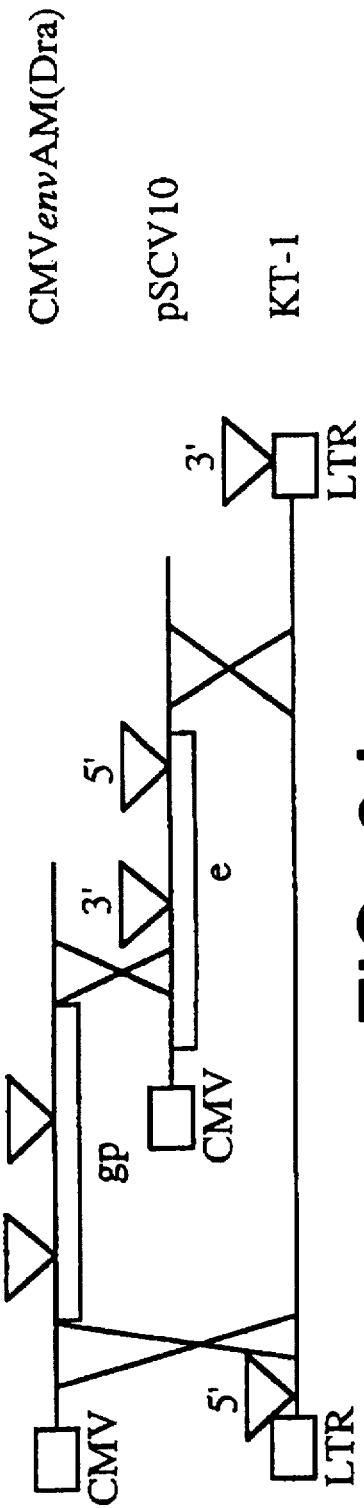

The terms defined below are used throughout the specification and, unless otherwise indicated, shall be understood as defined below.

A "vector construct" according to this invention refers to a nucleic acid construct capable of directing the expression of viral proteins in a system for producing disabled viral vectors. In the case or retroviral vectors these are the gag/pol or env coding regions. Briefly, the vector construct encodes the structural polypeptides necessary to produce infectious recombinant virus. The vector comprises a gag/pol or env gene operably associated with a promoter, a polyadenylation signal and may contain one or more nucleic acid cassettes.

"Recombinant vector" refers to a nucleic acid construct capable of directing the expression of one or more coding region(s), or "gene(s)," of interest. Briefly, in the case of retroviral vectors, the recombinant vector must include a 5' LTR, a tRNA binding site, a packaging signal, one or more nucleic acid sequences encoding a gene of interest (i.e., heterologous sequences), an origin of second strand DNA synthesis, a 3' LTR or a portion thereof, and may include one or more nucleic acid cassettes. A wide variety of heterologous sequences may be included within the recombinant vector, including, for example, sequences which encode a protein (e.g., a cytotoxic protein, an immune accessory molecule, or a replacement protein such as factor VIII for a patient suffering from hemophilia) or nucleic acid sequences (e.g., a ribozyme or an antisense sequence). Alternatively, the heterologous sequence may merely be a "filler" or "stuffer" fragment of a size sufficient to allow production of viral particles containing the RNA genome.

As used herein, a "nucleic acid cassette" refers to a nucleic acid molecule which comprises a sequence encoding a non-biologically active inhibitory molecule and one or more polynucleotides useful in joining various nucleic acids of interest such that the cassette may be easily inserted into a vector. Typically this is accomplished by placing one or more restriction sites at the 5' and/or the 3' ends of the cassette. In addition to the components already described, the cassette may also contain a splice site located 3' or 5' to the nucleic acid sequence encoding the inhibitory molecule. Examples of splice site gene sequences that may be used in the nucleic acid cassette include those from SV40 or the human β-globin gene (Lawn et. al., Cell 21:647, 1980) and the like.

An "inhibitory molecule" according to this invention may be a toxic polypeptide, a prodrug activating enzyme, or a ribozyme, the expression of which results from one or more recombination events between the various vectors of the invention. The resultant inhibitory molecule may function directly or indirectly to poison the cell in which it is expressed or may act to prevent assembly of the viral particle. Alternatively, the inhibitory molecule may be a ribozyme which cleaves the viral genome or any of the transcribed viral messenger RNA required for the production of retroviral particles designed to function as described herein. As those in the art will appreciate, a wide variety of inhibitory molecule nucleic acid sequences may be included in the nucleic acid cassette, for example, ricin (Lamb et al., Eur. J. Biochem. 148:265, 1985), abrin (Wood et al., Eur. J. Biochem. 198:723, 1991; Evensen, et al., J. of Biol. Chem. 266:6848, 1991; Collins et al., J. of Biol. Chem. 265:8665, 1990; Chen et al., Fed. of Eur. Biochem Soc. 309:115, 1992), diphtheria toxin (Yamaizumi et al., Cell 15:245, 1978 Leong, et al., J. Bacteriol. 163:1114, 1985 Greeenfield et al., PNAS 80:685, 1983; Tweten et al., J. Biol. Chem. 260:10392, 1985), cholera toxin (Mekalanos et al., Nature 306:551, 1983; Sanchez & Holmgren, PNAS 86:481, 1989), gelonin (Stirpe et al., J. Biol. Chem. 255:6947, 1980), pokeweed (Irvin, Pharmac. Ther. 21:371, 1983), antiviral protein (Barbieri et al., Biochem. J. 203:55, 1982; Irvin et al., Arch. Biochem. & Biophys. 200:418, 1980; Irvin, Arch. Biochem. & Biophys. 169:522, 1975), tritin, Shigella toxin (Calderwood et al., PNAS 84:4364, 1987; Jackson et al., Microb. Path. 2:147, 1987), and Pseudomonas exotoxin A (Carroll and Collier, J. Biol. Chem. 262:8707, 1987), tetanus (Eisel, et al., EMBO 5:2495, 1986 and Fairweather, et al., J. Bacter. 165:21, 1986) herpes thymidine kinase (Becker, et al., Gene 21:51, 1983; Wagner, et al., PNAS 78:1441, 1981), and E. coli gpt (Faulkner, et al., Journal of Virology 62:1849, 1988; Jagadeeswaran, et al., Gene 31:309, 1984).

A nucleic acid molecule encoding a "non-biologically active" inhibitory molecule refers to a nucleic acid molecule that is less than the complete nucleotide sequence coding for the inhibitory molecule. Expression of such a sequence will result in loss of greater than 80% of the activity of the inhibitory molecule as measured in vitro. As a consequence, the resultant inhibitory molecule, whether a polypeptide or ribozyme, will not be toxic directly or indirectly to cells in which it is produced.

DETAILED DESCRIPTION OF THE INVENTION

The present invention provides an improved mechanism to prevent the production of replication competent virus when packaging cell lines are transfected with a recombinant retrovector. As discussed previously, genetic interactions between the DNA within packaging cells, which includes the packaging cell genome, the helper virus genome(s), and the retroviral vector (i.e., the recombinant vector) may result in recombination events which may lead to the production of replication competent virus. According to this invention, the spread of replication competent retrovirus generated through such recombination events may be prevented by providing vectors encoding a non-biologically active inhibitory molecule which produces a nucleic acid molecule encoding a biologically active inhibitory molecule upon recombination. The expression of this molecule prevents viral production of a replication competent retrovirus either by killing the producer cell(s) in which that event occurred or by suppressing production of the retroviral vectors therein. Alternatively, the complete nucleic acid sequence of the inhibitory molecule may not be required to reconstitute biological activity. In fact, any nucleic acid sequence which produces a biologically active inhibitory molecule upon recombination is acceptable. In addition, it is not necessary that full biological activity be restored. Any activity constituting inhibition of the production of replication competent virus is acceptable. Such inhibition may be determined through the use of the *Mus dunni* co-cult assay (see Example 6). A variety of inhibitory molecules may be used, including ribozymes, which cleave the RNA transcript of the replication competent virus, or a toxin such as ricin A, tetanus, or diphtheria toxin, herpes thymidine kinase among others.

A variety of methods may be used to identify non-biologically active nucleic acid fragments of inhibitory molecules that may be incorporated into nucleic acid cassettes. The nucleic acid cassettes of the invention comprise a nucleic acid sequence of a non-biologically active inhibitory molecule, 3' and 5' restriction site polynucleotide sequences, and may optionally contain a splice site. These nucleic acid cassettes are synthesized using standard recombinant methods, including solid state DNA synthesis (see Caruthers et al., *Method in Enzymology* 211:3, 1992). The non-biologically active inhibitory molecule is encoded by a nucleic acid molecule derived from a nucleic acid coding for an active form of the same molecule. In order to produce the non-biologically active form, the gene encoding the active compound has been divided into fragments such that each fragment encodes a non-biologically active molecule. These fragments are synthesized (or cloned) and incorporated into separate nucleic acid cassettes. The cassettes are inserted into separate vectors at locations near regions of homology between the vectors.

Activity of inhibitor molecules can be measured in vitro. For example in the case of diphtheria toxin, toxicity may be tested using the NAD/EF-2 ADP-ribosyl transferase assay (Wilson et al., *Biochemistry* 29:8643, 1990). The diphtheria toxin nucleotide sequence has been determined. Thus, the polypeptides it encodes can be systematically truncated, by engineering the gene to systematically delete 5' and 3' regions. Alternatively, exonuclease digestion can be similarly employed to truncate the gene from either the 5' or 3' end. After systematically generating truncated genes, the digested fragments can be inserted into an appropriate expression vector. The resultant protein is then tested in an activity assay to determine what, if any, activity remains. For instance, a toxicity assay such as that described by Fischer et al., (*Infectious Immunity*, 59:3562, 1991) using co-transfection of a diphtheria toxin expression vector and a reporter expression vector, for example, expressing the luciferase gene, can be utilized to determine activity of the diphtheria toxin fragment. As those in the art will appreciate, other similar assays can be used to test the activity of other toxins following truncation of their corresponding genes. Where the molecule is a prodrug activating enzyme such as HSVTK (Wagner et al., *PNAS* 78:1441, 1981), the HSVTK can be truncated and tested for activity by its ability to make TK⁻ cells resistant to hypoxanthine aminopterin thymidine (HAT) selection (Bacchetti et al., *PNAS* 74:1590, 1977) or allowing TK⁻ cells to incorporate $^3$H thymidine.

Ribozymes are RNA molecules with enzymatic activity used to cleave other RNA molecules. They consist of short RNA sequences possessing highly conserved sequence-specific cleavage domains with catalytic activity flanked by regions complementary to the target sequence which allow accurate positioning of the enzyme relative to the cleavage site in the desired target molecule. They are highly flexible tools for inhibiting the expression and activation of specific genes (Haseloff et al., *Nature*, 334:585, 1988). Custom ribozymes can be designed by selecting the particular target RNA sequence to be cleaved. Complementary sequences are synthesized and placed at the beginning and end of the ribozyme coding sequence. The resulting ribozyme will only cleave RNA molecules containing that specific sequence.

The 3' and 5' restriction site polynucleotide sequences are provided for ease of insertion into a desired expression vector. A variety of linker sequences may be used, however preferred linker sequences are those having complementary sequences to restriction sites available for insertion purposes within desired expression vectors.

To assure that the recombination event results in the joining of these fragments such that a biologically active molecule is produced, one or more splice sites may be incorporated into the nucleic acid cassette. Splice sites are specific nucleotide sequences located in genes that are used to join (i.e., splice) genomic exon sequences and eliminate intron sequences during post-transcriptional RNA processing. The 5' and complementary 3' nucleotide sequences of a splice site are generally separated by a region which is eliminated during the splicing event. The use of splice sites assures selective joining of the non-biologically active inhibitory molecule nucleic acid sequences such that upon translation a biologically active inhibitory molecule is produced. A variety of splice sites may be used in the present invention, including splice sites derived from SV40 and the human β-globin gene, among others.

The nucleic acid cassettes of the present invention may be inserted into the gag/pol and env vector constructs of the packaging cell as well as into the recombinant vector.

The present invention also provides a variety of gag/pol expression vectors containing one or more of the nucleic acid cassettes described previously. Such expression vectors encode the structural polypeptides necessary to produce infectious recombinant retrovirus. Introduction of such vectors into a cell line results in the production of the packaging cell lines. Each of these vectors comprise a gag/pol gene operably associated with a promoter, a polyadenylation signal and one or more nucleic acid cassettes of the invention. Briefly, the gag/pol gene contains a gag region which encodes a variety of structural proteins that comprise the viral core matrix and nucleocapsid proteins, and a pol region which encodes a protease for the processing of viral structural polypeptides such as gag/pol and env proteins, a reverse transcriptase, an RNase H, and an integrase, which is required for integration of the retroviral vector into the host genome. A variety of gag/pol genes may be utilized in the gag/pol vector, for example the gag/pol gene may be derived from the retroviruses MoMLV (Miller et al., *Mol. Cell Biol.* 5:531, 1985), 4070A (Cone and Mulligan, *PNAS* 81:6349, 1984), HTLV I (Wilson et al., *J. Vir.* 63:2374, 1989), HIV (Rather, et. al., *Nature* 313:277, 1985), MPMV (GB 2,269,175A and WO 93/17118), SRV-I (Heidecher et al., *J. Vir.* 61:3066, 1987), HFV or MFV (Mourer et al., *J. Vir.* 62:1590, 1988), GALV (O'Hara et al., *Cell Growth and Differentiation* 3:119, 1990), BLV (Ban et al., *J. Gen. Vir.* 70:1987, 1989), FeLV (Laprevotte et al., *J. Vir.* 50:884, 1984) and FIV (Talbott et al., *PNAS* 86:5743, 1989).

Within other aspects of the present invention, a variety of env expression vectors are provided which comprise one or more nucleic acid cassettes described above. More specifically, an env vector according to the invention comprises an env gene which optionally may be operably associated with a promoter, a polyadenylation signal and one or more of the nucleic acid cassettes described previously. Briefly, the env gene encodes two principle proteins, the surface glycoprotein "SU" and the transmembrane protein "TM" (Stevenson, et. al., *AIDS Res. Hum. Retro.* 8:107, 1992). In the case of retroviruses, a third protein of undetermined function, designated the "R peptide," is also expressed from the env gene.

A variety of env genes may be utilized in the vector, including, for example, an env gene derived from the retroviruses MoMLV, 4070A, HTLV I, HTLV-II, HIV, MPMV, SRV-1, HFV, MFV, SIV, GALV, BLV, FeLV and FIV, although env genes derived from other sources may also be employed. After expression and virion assembly, the portion of the env protein presented on the viral surface may be recognized by cell surface receptors, thereby permitting viral binding and subsequent infection of the cell. The affinity for binding different cell types may be increased by expression of amphotropic, xenotropic or polytropic env proteins. In general, amphotropic viruses have a broad range host range and replicate in both homologous and heterologous cells. In addition, they do not demonstrate cross interference or cross neutralization with ecotropic and xenotropic viruses. Unlike amphotropic viruses, xenotropic viruses are endogenous to one species, but cannot replicate well in that species due to lack of specific receptors on the cells of its host. However, polytropic viruses can replicate in both homologous and heterologous cells but unlike amphotropic viruses they are neutralized by antiserum to the major glycoprotein, gp70, of both ecotropic and xenotropic MLVs. For example, a cell that lacks an receptor is more resistant to infection with an viral particle containing amphotropic env; however, a cell expressing the receptor can be infected more easily by a viral particle containing xenotropic env. The construction of packaging cell lines that express the amphotropic, xenotropic and polytropic env proteins is described in patent application WO 92/05266, which is hereby incorporated by reference.

The vectors described above preferably contain an env and/or gag/pol gene operably associated with a promoter. It will be evident by one skilled in the art that the promoter may be an endogenous promoter or supplied by the retrovector. A variety of promoters may be used to direct the expression of these proteins including an RSV promoter (Ruker et al., *Ann. N.Y. Acad. Sci.* 646:212, 1991), an adenovirus major late promoter (MLP) (Chanda et al., *Virology* 175:535, 1990), and an SV40 promoter (Bird et al., *Aids Res and Human Retroviruses* 8:1999, 1992). A preferred promoter is the CMV MIE promoter (Stinski et. al., *J. Vir.* 46:1, 1983). In those instances where no promoter is included the retroviral vector, it is envisioned that integration into the host's genome will provide the requisite regulatory and expression control elements, preferably by a recombination event which places the structural gene construct adjacent to a desired promoter in an operable fashion.

The present invention further provides recombinant vectors in a variety of viral vector packaging systems in which one or more essential functions of the parent virus has been deleted so that it is deficient in some function (e.g., genome replication), but retains a packaging signal and the ability to express a heterologous inserted gene sequence (the "gene of interest"). The deleted essential function or functions are provided by packaging cells into which the vector genome can be introduced to yield producer cell lines that then make replication defective viral particles encapsidating the recombinant vector. The recombinant vector may further contain one or more nucleic acid cassettes described above. The vector genome is then introduced into target cells by an infection event but is incapable of further propagation. In any such situation, it is important to prevent the recombination of the various parts of the virus in a producer cell line to give replication competent virus genomes, or to eliminate cells in which this occurs. Many such vectors, packaging cells and producer cells, may be constructed from a variety of viruses, including for example, poliovirus (Evans et al., *Nature* 339:385, 1989, and Sabin et al., *J. of Biol. Standardization* 1:115, 1973) (ATCC VR-58); rhinovirus (Arnold et al., *J. Cell. Biochem.* L401, 1990) (ATCC VR-1110); pox viruses, such as canary pox virus or vaccinia virus (Fisher-Hoch et al., *PNAS* 86:317, 1989; Flexner et al., *Ann. N.Y. Acad. Sci.* 569:86, 1989; Flexner et al., *Vaccine* 8:17, 1990; U.S. Pat. No. 4,603,112 and U.S. Pat. No. 4,769,330; WO 89/01973) (ATCC VR-111; ATCC VR-2010); SV40 (Mulligan et al., *Nature* 277:108, 1979) (ATCC VR-305), (Madzak et al., *J. Gen. Vir.* 73:1533, 1992); influenza virus (Luytjes et al., *Cell* 59:1107, 1989; McMicheal et al., *The New England Journal of Medicine* 309:13, 1983; and Yap et al., *Nature* 273:238, 1978) (ATCC VR-797); adenovirus (Berkner et al., *Biotechniques* 6:616, 1988, and Rosenfeld et al., *Science* 252:431, 1991) (ATCC VR-1); parvovirus such as adeno-associated virus (Samulski et al., *J. Vir.* 63:3822, 1989, and Mendelson et al., *Virology* 166:154, 1988) (ATCC VR-645); herpes simplex virus (Kit et al., *Adv. Exp. Med. Biol.* 215:219, 1989) (ATCC VR-977; ATCC VR-260); *Nature* 277: 108, 1979); HIV (EPO 386,882, Buchschacher et al., *J. Vir.* 66:2731, 1992); measles virus (EPO 440,219) (ATCC VR-24); Sindbis virus (Xiong, et al., *Science* 234:1188, 1989) and coronavirus (Hamre et al., *Proc. Soc. Exp. Biol. Med.* 121:190, 1966) (ATCC VR-740). In particular, such vectors, packaging cells and producer cells, may be constructed from a variety of retroviruses including, avian leukosis virus (ATCC Nos. VR-535 and VR-247), BLV (VR-1315), MLV, mink-cell focus-inducing virus (Koch et al., *J. Vir.* 49:828, 1984; and Oliff et al., *J. Vir.* 48:542, 1983), murine sarcoma virus (ATCC Nos. VR-844, 45010 and 45016), reticuloendotheliosis virus (ATCC Nos VR-994, VR-770 and 45011) and rous sarcoma virus (ATCC Nos VR-772, VR-354, VR-270, VR-724 and VR-725). Particularly preferred retroviruses are murine leukemia viruses 4070 A and 1504 A (Hartley, *J. Vir.* 19:19, 1976), Abelson (ATCC No. VR-999), Friend (ATCC No. VR-245), Graffi (Ru et al., *J. Vir.* 67:4722, 1993; and Yantchev *Neoplasma* 26:397, 1979), Gross (ATCC No. VR-590), Kristen (Albino et al., *J. Exp. Med.* 164:1710, 1986), Harvey sarcoma virus (Manly et al., *J. Vir.* 62:3540, 1988; and Albino et al., *J. Exp. Med.* 164:1710, 1986) and Raucher (ATCC No. VR-998) and Moloney leukemia virus (ATCC No. VR-190). Particularly preferred non-mouse retroviruses are rous sarcoma viruses, Bratislava, (Copeland et al., *J. Neuropath. Exp. Neurology* 34:N1, P100, 1975), Bryan high titer (e.g., ATCC Nos. VR-334, VR-657, VR-726, VR-659, and VR-728), Bryan standard (ATCC No VR-140), Carr-Zilber (Adgighitov et al., *Neoplasma* 27:159, 1980, Engelbreth-Holm-Swarm (Laurent et al., *Biochem Biophys Acta* 908:241, 1987), Harris, Prague (ATCC Nos. VR-772 and 45033), Schmidt-Ruppin (e.g., ATCC Nos. VR-724, VR-725, and VR-354). The expression vector may be readily assembled from any virus or retrovirus utilizing standard recombinant techniques (e.g., Sambrook et. al.,

*Molecular Cloning: A Laboratory Manual*, 2d ed. Cold Spring Harbor Laboratory Press, 1989), Further description of the construction of retroviral vectors is described in U.S. Ser. No. 07/586,603, now abandoned, herein incorporated by reference.

Within a preferred aspect of the present invention the recombinant vector is a Sindbis recombinant vector construct. Sequences encoding wild type Sindbis virus suitable for use in preparing the vector constructs and particles may be readily obtained from naturally occurring sources or from depositories (e.g., the American Type Culture Collection, Rockville, Md.). An infectious Sindbis cDNA clone is obtained by linking the 5' RNA end of a Sindbis virus cDNA clone to a bacteriophage RNA polymerase promoter, and the 3' end of the cDNA clone to a poly-adenosine sequence of approximately 25 nucleotides. This infectious cDNA clone may be readily utilized to prepare a recombinant Sindbis vector construct. The recombinant Sindbis vector construct comprises a 5' sequence capable of initiating transcription of a Sindbis virus, a nucleotide sequence encoding Sindbis non-structural proteins (e.g. NSP1, NSP2, NSP3, or NSP4), a viral junction region which has been modified (i.e. as measured by a RNase protection assay) such that viral transcription of the subgenomic fragment is reduced, a Sindbis RNA polymerase recognition sequence, a heterologous gene sequence or "gene of interest", may contain one or more nucleic acid cassettes described above and may contain a 3' sequence which controls transcription termination. Within another embodiment of the invention, the viral junction region may be in tandem such that the first viral junction region which has been inactivated and a second viral junction region which has been modified to reduce the viral transcription of the subgenomic fragment. A retroviral packaging sequence may be inserted into the tandem vector, and located between the first (inactivated) viral junction region, and the second, (modified) viral junction region in order to increase the efficiency of Sindbis vector transfer into a Sindbis packaging cell line. The construction of Sindbis vector are further described in U.S. Ser. No. 08/198,450, now abandoned, hereby incorporated by reference.

Since the various nucleotide sequences required for generating therapeutically useful retroviral vectors are typically harbored on more than one nucleic acid molecule and frequently contain homologous regions between the vectors, consequently, recombination may occur between the nucleotide sequences of retroviral gag/pol and env and other nucleic acid sequences that are conserved among the various vectors present in the packaging and/or producer cells. For example, in the vector producing cell line DAKT-1 homologous regions are present in the gag/pol expression vector pSVC10 from about nucleotide positions 5,482 to 7,019 and in the amphotropic env expression vector CMVenvAm(Dra) from about nucleotide positions 1,714 to 2,255. Consequently, a suitable 5' inhibitor 5' splice nucleic acid cassette may be inserted 5' of the homologous region in the gag/pol expression vector pSCV10 and a 3' splice 3' inhibitor nucleic acid cassette may be inserted 3' of the homologous region in the amphotropic env expression vector CMVenvAm(Dra), so that a homologous recombination event will result in the production of a nucleic acid molecule containing both the 5' inhibitor/5' splice and the 3' splice/3' inhibitor nucleic acid cassettes which could induce splicing between the 2 nucleic acid cassettes and restore the coding sequence for a biologically active inhibitory molecule.

As noted above, the recombinant vectors may contain and express one or more nucleic acid sequences encoding a "gene of interest," a so-called "heterologous" sequence. A wide variety of heterologous sequences may be used within the context of the present invention, including nucleic acid sequences encoding, for example, a cytotoxic protein, an antisense molecule, a gene product that activates a compound with little or no cytotoxicity (i.e., a "prodrug") into a toxic product, an immunogenic portion of disease-associated antigen, an immune accessory molecule, or replacement protein.

Within further embodiments of the invention, an antisense molecule may be used in order to induce a potent MHC Class I restricted response. Briefly, an antisense molecule binds to a complementary sequence of an RNA, typically an mRNA, to form a double stranded complex, thereby preventing translation. In addition, the formation of large quantities of double-stranded RNA resulting from the expression of high levels of specific antisense sequences may be utilized to induce the increased expression of interferons (e.g., gamma-interferon (γ-IFN)). The increased expression of γ-IFN, in turn, boosts the expression of MHC Class I antigens (Shiloni et al., *Cancer Immunology Immunotherapy* 37:286, 1993). Preferred antisense sequences include those complementary to actin RNA (Hanauer et al., *Nucleic Acids Res.* 11:3503, 1983; Gunning et al., *Mol. Cell. Bio.* 3:787, 1983; Khalili et al., *Gene* 21:9, 1983, myosin RNA (Gunning et al., *Mol. Cell. Bio.* 3:787, 1983), and histone RNA.

A further embodiment of the invention employs antisense sequences that inhibit tumor cell growth, viral replication, or a genetic disease by preventing the cellular synthesis of proteins required for cell growth, maintenance and/or propagation. Examples of such antisense molecules include those complementary to a nucleic acid sequence of thymidine kinase, dihydrofolate reductase (Maher and Dolnick, *Arch. Biochem. & Biophys.* 253:214, 1987; Bzik et al., *PNAS* 84:836, 1987), HER2 (Coussens et al., *Science* 230:1132, 1985), antisense ABL (Fainstein, et al., *Oncogene* 4:1477, 1989), Myc (Stanton et al., *Nature* 310:423, 1984) and ras, as well as antisense sequences which block one or more of the enzymes in the nucleotide biosynthetic pathway.

In yet another aspect of the invention, recombinant vectors are provided which direct the expression of a heterologous sequence that activates a compound with little or no cytotoxicity (i.e., a "prodrug") into a toxic product. Representative examples of such heterologous sequences include varicella zoster virus thymidine kinase (VZVTK), herpes simplex virus thymidine kinase (HSVTK) (Field et al., *J. Gen. Virol.* 49:115, 1980), and *E. coli.* guanine phosphoribosyl transferase (see U.S. patent application Ser. No. 08/155,944, entitled "Compositions and Methods for Utilizing Conditionally Lethal Genes," filed Nov. 18, 1993; see WO 93/10218 entitled "Vectors Including Foreign Genes and Negative Selection Markers", WO 93/01281 entitled "Cytosine Deaminase Negative Selection System for Gene Transfer Techniques and Therapies", WO 93/08843 entitled "Trapped Cells and Use Thereof as a Drug", WO 93/08844 entitled "Transformant Cells for the Prophylaxis or Treatment of Diseases Caused by Viruses, Particularly Pathogenic Retroviruses", and WO 90/07936 entitled "Recombinant Therapies for Infection and Hyperproliferative Disorders", all of which are herein incorporated by reference). In a preferred embodiment of the invention, such recombinant vectors direct the expression of a heterologous sequence that converts a prodrug into a toxic product in the presence of a pathogenic agent, thereby affecting localized therapy to the pathogenic agent (see U.S. Ser. No. 08/155,944, now abandoned, incorporated herein by reference).

Also within the scope of the invention are recombinant vectors which direct the expression of a prodrug activating gene (e.g., the HSVTK gene) under the control of an HIV expression system (i.e., one that is inactive unless activated by HIV tat protein). Expression of the tat gene product in human cells infected with HIV and carrying such a vector will result in increased production of HSVTK. The cells (either in vitro or in vivo) are then exposed to a drug such as ganciclovir, acyclovir or its analogs (e.g., fluoroarabinoside uridine (FIAU) or fluoroarabinoside cytodine (FIAC)). Such drugs are known to be phosphorylated by HSVTK (but not by cellular thymidine kinase) to their corresponding biologically active nucleotide triphosphate forms. Acyclovir and FIAU triphosphates inhibit cellular polymerases in general, leading to the specific deterioration and death of cells expressing HSVTK in transgenic mice (Borrelli et al., PNAS 85:7572, 1988). Thus, cells containing the recombinant vector and expressing HIV tat protein will be selectively killed.

In another aspect of the present invention, recombinant vectors are provided which direct expression of a prodrug activating gene under control of a pathogenic-specific, tumor-specific or gene specific expression control system such as a promoter locus control region or translational control region. In this case the prodrug activating enzyme will be different and independent of the anti-recombination prodrug system in the packaging cell line, so that selection with the prodrug against recombination does not also select against the vector encoded prodrug.

In another aspect of the present invention, a recombinant vector may also direct the expression of one or more nucleic acid sequences which encode immunogenic portions of disease-associated antigens. Antigens are considered to be "immunogenic" if they are capable of causing an immune response (either cell-mediated or humoral) under appropriate conditions. Immunogenic "portions" are variable in size, but are preferably at least nine amino acids long, and may be sufficiently large so as to include the entire antigen. As utilized within the context of the present invention, antigens are said to be "disease-associated" if they are either associated with rendering a cell (or organism) diseased or are associated with the disease state in general but are not required or essential for rendering the cell diseased.

A wide variety of "disease-associated" antigens are contemplated within the scope of the present invention including, for example, immunogenic, non-tumorigenic forms of altered cellular components normally associated with tumor cells (see U.S. Ser. No. 08/104,424, now abandoned, herein incorporated by reference). Representative examples of altered cellular components normally associated with tumor cells include ras* (wherein "*" is understood to refer to antigens that have been altered to be non-tumorigenic) (Kumar et al., Science 248:1101, 1990), p53* (Linzer and Levine, Cell 17:43, 1979; Lane and Crawford, Nature 278:261, 1979; Hinds et al., J. Vir. 63:739, 1989; and Levine et al., Nature 453:1991), Rb* (Friend et al., Nature 323:643, 1986; Lee et al., Science 235:1394, 1987; and Fung et al., Science 236:1657, 1987), altered protein encoded by Wilms' tumor gene (Call et al., Cell 60:509, 1990; Gessler et al., Nature 343:744, 1990; Rose et al., Cell 60:495, 1990; and Haber et al., Cell 61:1257, 1990), ubiquitin* (Lund et al., J. Biol. Chem. 263:4926, 1985; and Mafune et al., Arch. Surg. 126:462, 1991), mucin (Girling et al., Int. J. Cancer 43:1072, 1989; Gendler et al., J. Biol. Chem. 265:15286, 1990, Lan et al., J. Biol. Chem. 265:15294, 1990; Ligtenberg et al., J. Biol. Chem. 265:5573, 1990; and Jerome et al., Cancer Res. 51:2908, 1991), protein encoded by the DCC (Fearon et al., Science 247:49, 1990), APC and MCC (Kinzler et al., Science 251:1366, 1991) genes, as well as receptors or receptor-like structures such as neu (Salmon et al., Science 244:707, 1989; Salmon et al., Cancer Cells 7:371, 1989; Shih et al., Nature 290:261, 1981; Schechter et al., Nature 312:513, 1984; and Coussens et al., Science 230:1132, 1985), thyroid hormone receptor (Nakai et al., Mol. Endocrin. 2:1087, 1988; Pfahl et al., Nucleic Acids Res. 15:9613, 1987; Benbrook et al., Science 238:788, 1987), platelet derived growth factor ("PDGF") receptor (Giebel et al., Amer. J. Human Genetics 49:406, 1991), insulin receptor (Newman et al., Inter. J. of Cancer 44:467, 1989; Zick Crit. Rev. Biochem. and Mol. Bio. 24:217, 1989; Goldstein et al., Clin. Res. 37:570, 1989), epidermal growth factor ("EGF") receptor (Vanagothoven et al., Cancer Research 52:5082, 1992), and the colony stimulating factor ("CSF") receptor (Larsen et al., J. Exp. Med. 172:1559, 1990; Gearing et al., EMBO J. 8:3667, 1989).

"Disease-associated" antigens should also be understood to include all or portions of various eukaryotic, prokaryotic or viral pathogens. Representative examples of viral pathogens include the hepatitis B virus ("HBV") and hepatitis C virus ("HCV"; see U.S. Ser. No. 08/102,132, now abandoned), human papilloma virus ("HPV"; see WO 92/05248; WO 90/10459; EPO 133,123), Epstein-Barr virus ("EBV"; see EPO 173,254; JP 1,128,788; and U.S. Pat. Nos. 4,939,088 and 5,173,414), FeLV (see U.S. Ser. No. 07/948, 358, now abandoned, EPO 377,842; WO 90/08832; WO 93/09238), FIV (see U.S. Pat. No. 5,037,753; WO 92/15684; WO 90/13573; and JP 4,126,085), HTLV I and II (Poiesz et al., PNAS 77:7415, 1980; Reitz et al., Vir. 26:688, 1983; Popovic et al., Science 219:856, 1983; Gallo et al., Cancer Surveys eds. Oxford University Press 113, 1984), and HIV (see U.S. Ser. No. 07/986,084, now abandoned).

Within another aspect of the present invention, recombinant vectors may also direct the expression of one or more immune accessory molecules. Accessory molecules are molecules that can either increase or decrease the recognition, presentation or activation of an immune response, be it cell-mediated or humoral. Representative examples of immune accessory molecules include alpha-interferon (α-IFN) (Ogasawara et al., Cancer Research 53:3561, 1993), beta-interferon (β-IFN) (Lauret et al., Human Gene Therapy 4:567, 1993), γ-IFN (Ogasawara et al., Cancer Research 53:3561, 1993), IL-1 (Furutani et al., Nucleic Acids Res. 14:3167, 1986; Gubler et al., J. Immun. 136:2492, 1986), IL-2, IL-3 (Lokker et al., EMBO 10:2125, 1991; Lokker et al., J. Biol. Chem. 266:10624, 1991), IL-4 (Lotze et al., Human Gene Therapy 5:41, 1994; and Hunt et al., J. Immunotherapy 14:314, 1993), IL-5 (Desreumaux et al., J. Exp. Med. 175:293, 1992), IL-6 (Matsuura et al., Ann. New York Acad Sci., 557:122, 1989; Vandamme Ann. New York Acad. Sci. 557:104, 1989), IL-7 (U.S. Pat. No. 4,965,195), IL-8, IL-9, IL-10 (Spits et al., Int. Arch. Allergy and Immun. 99:8, 1992), IL-11 (Paul et al., Exp. Hematology 22:295, 1994; and Hawley et al., J. Exp. Med. 178:1175, 1993), IL-12 (Wolf et al., J. Immun. 46:3074, 1991; Gubler et al., PNAS 88:4143, 1991; WO 90/05147; EPO 433,827), IL-13 (WO 94/04680), GM-CSF (Miyatake et al., EMBO J. 4:2561, 1985), M-CSF-1 (Kawasaki, et al., Science 230:291, 1985), G-CSF (Nagata et al., Nature 319:415, 1986), CD3 (Krissanen et al., Immunogenetics 26:258, 1987), CD8 (Nakayama, et al., J. Immun. 148:1919, 1992), ICAM-1 (Simmons et al., Nature 331:624, 1988), ICAM-2 (Singer, Science 255:1671, 1992), β-microglobulin (Parnes et al., PNAS 78:2253, 1981), LFA-1 (Altmann et al., Nature 338:521, 1989), LFA3 (Wallner et al., J. Exp. Med. 166(4) :923, 1987), HLA Class I, HLA Class II molecules, B7 (Freeman et al., J. Immun. 143:2714, 1989), and B7-2 (Freemen et al., Science 262:909, 1993).

In another embodiment, the recombinant vector expresses an agent that suppresses an immune response within an animal. Suppression of an immune response may be beneficial in preventing graft rejection, destruction of therapeutic agents provided by gene therapy in the treatment of genetic disorders (e.g., thalassemia, phenylketonuria, Lesch-Nyhan syndrome, severe combined immunodeficiency (SCID), hemophilia A and B, cystic fibrosis, Duchenne's muscular dystrophy, inherited emphysema, familial hypercholesterolemia and Gaucher's disease) and autoimmune responses (e.g., multiple sclerosis, rheumatoid arthritis, diabetes and uveitis). More specifically, the recombinant vector will suppress immunity by directing the expression of a protein or active portion of a protein that binds intracellularly to newly synthesized MHC class I molecules. This binding prevents migration of the MHC class I molecule from the endoplasmic reticulum, resulting in the inhibition of terminal glycosylation. This blocks transport of these molecules to the cell surface and prevents cell recognition and lysis by cytotoxic T-lymphocytes (CTLs). For instance, one of the products of the E3 gene (Herisse et al., *Nucleic Acids Res.* 8:2173, 1980 and Cladaras et al., *Vir.* 140:28, 1985) may be used to inhibit transport of MHC class I molecules to the surface of the transformed cell. More specifically, E3 encodes a 19 kD transmembrane glycoprotein, E3/19K, transcribed from the E3 region of the adenovirus 2 genome. Within the context of the present invention, tissue cells are transformed with a recombinant vector containing the E3/19K nucleic acid sequence. These transformed cells are then able to evade an immune response upon production of the E3/19K protein.

Within another embodiment of the present invention, the recombinant vector directs the expression of a protein or an active portion of a protein capable of binding $\beta_2$-microglobulin. Alternatively, the expression of $\beta_2$-microglobulin can be inhibited by antisense RNA or by a ribozyme specifically reactive against its mRNA. Briefly, the transport of MHC class I molecules to the cell surface for antigen presentation requires association with $\beta_2$-microglobulin. As a result, proteins that bind $\beta_2$-microglobulin and inhibit its association with MHC class I indirectly inhibit MHC class I antigen presentation. Suitable inhibiting proteins include the H301 gene product. Briefly, the H301 gene, obtained from the human cytomegalovirus (CMV), encodes a glycoprotein with sequence homology to the $\beta_2$-microglobulin binding site on the heavy chain of the MHC class I molecule (Browne et al., *Nature* 347:770, 1990). H301 binds $\beta_2$-microglobulin, thereby preventing the maturation of MHC class I molecules, and renders transformed cells unrecognizable by CTLs, thus evading MHC class I restricted immune surveillance. Particularly preferred methods of preventing graft rejection are described in "Methods for Suppressing Graft Rejection" (U.S. Ser. No. 08/116,827, now abandoned, herein incorporated by reference). Preferred methods of preventing immune responses against therapeutic agents for the treatment of genetic diseases are described in "Methods of Suppressing Immune Responses by Gene Therapy" (U.S. Ser. No. 08/116,828, now abandoned, herein incorporated by reference) and preferred methods of preventing autoimmune responses are described in "Methods of Suppressing Autoimmune Responses" (U.S. Ser. No. 08/116,983, now abandoned, herein incorporated by reference).

In another aspect of the present invention, recombinant vectors may direct the expression of more than one heterologous sequence. Such multiple sequences may be controlled either by a single promoter (whether it is present in the vector or in the genome into which the vector is integrated), or preferably, by one or more additional promoters and may also include internal ribosome binding sites ("IRBS") in the event polycistronic messages are employed. Briefly, the upstream untranslated region of the immunoglobulin heavy chain binding protein has been shown to support the internal engagement of a bicystronic message. This sequence is small, approximately 300 bp, and may readily be incorporated into a vector in order to express multiple genes from a multicistronic message whose cistrons begin with this sequence (Jacejak and Sarnow, *Nature* 353:90, 1991).

In a preferred embodiment of the invention, recombinant vectors direct the expression of heterologous sequences that act synergistically. For example, recombinant vectors may direct the expression of an immune accessory molecule such as IL-12, IL-2, $\gamma$-IFN, or other molecule which acts to increase cell-mediated presentation in the $T_{H1}$ pathway along with an immunogenic portion of a disease-associated antigen. In such embodiments, immune presentation and processing of the disease-associated antigen will be increased due to the presence of the immune accessory molecule.

In another aspect of the invention, recombinant vectors are provided which direct the expression of one or more heterologous sequence(s) encoding "replacement proteins". The term "replacement proteins", as utilized in the present invention, refers to a therapeutic protein capable of preventing, inhibiting, stabilizing or reversing an inherited or non-inherited genetic defect. Such genetic defects include disorders in metabolism, immune regulation, hormonal regulation, and enzymatic or membrane associated structural function. Representative examples of diseases caused by such defects include cystic fibrosis ("CF"; see Dorin et al., *Nature* 326:614,), Parkinson's disease (Langston, *J. Neurol. Neurosurg. Psychiatry* 13 Supp. 1989), adenosine deaminase deficiency ("ADA"; Hahma et al., *J. Bact.* 173:3663, 1991), $\beta$-globin disorders (Kazazian et al., *Blood* 72:1107, 1988 and Francis et al., *Blood* 77:1405, 1991), hemophilia A and B (factor VIII-deficiencies; see Wood et al., *Nature* 312:330, 1984; Dieval et al., *Blood* 77:528, 1991 and Feinstein, *Blood* 60:284, 1982), Gaucher's disease (Barton et al., *N. Engl. J. Med.* 324:1464, 1991), diabetes (Bell, *Diabetes* 40:413, 1991 and Bell et al., *PNAS* 88:1484, 1991), forms of gouty arthritis and Lesch-Nylan disease (due to "HPRT" deficiencies; see Jolly et al., *PNAS* 80:477, 1983) and familial hypercholesterolemia (LDL receptor mutations; see Yamamoto et al., *Cell* 39:27, 1984).

Sequences which encode the above-described heterologous genes may be readily obtained from a variety of sources. For example, plasmids containing sequences that encode immune accessory molecules may be obtained from a depository such as the American Type Culture Collection (ATCC, Rockville, Md.), or from commercial sources such as British Bio-Technology Limited (Cowley, Oxford England). For example, sequences that may be obtained from such sources include BBG 12 (containing the GM-CSF gene coding for the mature protein of 127 amino acids), BBG 6 (which contains sequences encoding $\gamma$-IFN), ATCC No. 39656 (which contains sequences encoding TNF), ATCC No. 20663 (which contains sequences encoding $\alpha$-IFN), ATCC Nos. 31902, 31902 and 39517 (which contains sequences encoding $\beta$-IFN), ATCC No 67024 (which contains a sequence which encodes IL-1), ATCC Nos. 39405, 39452, 39516, 39626 and 39673 (which contains sequences encoding IL-2), ATCC Nos. 59399, 59398, and 67326 (which contain sequences encoding IL-3), ATCC No. 57592 (which contains sequences encoding IL-4), ATCC Nos. 59394 and 59395 (which contain sequences encoding IL-5), and ATCC No. 67153 (which contains sequences encoding IL-6). As will be evident to one of skill in the art, one may utilize either the entire sequence of the protein or an appropriate portion thereof which encodes the biologically active portion of the protein.

Alternatively, known cDNA sequences encoding cytotoxic genes or other heterologous sequences may be obtained from cells which express or contain such sequences. Briefly, within one embodiment of the invention, mRNA from a cell expressing the gene of interest is reverse transcribed with reverse transcriptase using oligo dT or random primers. The single-stranded cDNA may then be amplified by PCR (see U.S. Pat. No. 4,683,202, U.S. Pat. No. 4,683,195 and U.S. Pat. No. 4,800,159. See also PCR Technology: *Principles and Applications for DNA Amplification*, Erlich, Stockton Press, 1989, all of which are herein incorporated by reference) utilizing oligonucleotide primers complementary to sequences upstream or downstream of desired sequences. In particular, a double stranded DNA is denatured by heating in the presence of heat stable Taq polymerase, sequence specific DNA primers, and nucleotide bases dATP, dCTP, dGTP and dTTP. After annealing and elongation, double-stranded DNA is produced when synthesis is complete. This cycle may be repeated many times, resulting in an exponential amplification of the desired DNA.

Sequences which encode the above-described genes of interest may also be partially or completely chemically synthesized, for example, on an Applied Biosystems Inc. automated DNA synthesizer (e.g., ABI, DNA synthesizer model 392 (Foster City, Calif.)). Such genes may comprise a naturally occurring nucleotide sequence, an "optimized" nucleotide sequence based on codon preference, or combination(s) of the two.

The recombinant vectors described above can be used to generate transduction competent, and replication defective, viral particles by introducing them into appropriate packaging cell lines. A wide variety of animal cells may be utilized to prepare the packaging cells of the present invention, including for example, human, macaque, dog, rat and mouse cells. Preferentially, cell lines are selected that lack genomic sequences which are homologous to the retrovector construct, gag/pol expression cassette and env expression cassette to be utilized. Methods for determining homology may be readily accomplished by, for example, hybridization analysis (Martin, et al., *PNAS* 78:4892, 1981; and U.S. Ser. No. 07/800,921, now abandoned). Preferred packaging cell lines may be generated from Ψ2, D17 and HT1080 (Graham et al., *Vir.* 52:456, 1973), and 293 (Felgner et al., *PNAS* 84:7413, 1987).

Within another aspect of the present invention, methods are provided for producing packaging cell lines comprising a gag/pol vector and an env vector whose constructs are described above. A variety of packaging cell lines may be constructed that take advantage of the possible recombination events that result in the production of replication competent virus. These recombination events may occur between the recombinant vector and the gag/pol vector, between the gag/pol vector and the env vector, between the env vector and the recombinant vector or between all three vectors.

A packaging cell may be generated using a gag/pol vector containing a nucleic acid cassette comprising a nucleic acid sequence encoding a non-biologically active inhibitory molecule and an env vector that does not contain a nucleic acid cassette. A producer cell is generated by transduction of this packaging cell with recombinant vector containing a nucleic acid cassette. In the event of recombination within the 5' regions of the gag/pol vector and recombinant vector, the non-biologically active inhibitory molecule sequences are joined, resulting in a sequence which encodes a biologically active inhibitory molecule either directly or after an RNA splicing event. Alternatively, a packaging cell line may be generated using a env vector containing a nucleic acid cassette comprising a nucleic acid sequence encoding a non-biologically active inhibitory molecule and a gag/pol vector that does not contain a nucleic acid cassette. In the event of a recombination in the 3' regions of the env and recombinant vectors, the non-biologically active inhibitory molecule sequences are joined resulting in a sequence which encodes a biologically active inhibitory molecule, directly or indirectly. Further, a packaging cell line may be generated using the gag/pol vector and an env vector that each contain a nucleic acid cassette comprising a sequence encoding a non-biologically active inhibitory molecule. In the event of recombination in the region between Xba I and Sca I of the two vectors, the nucleic acid sequences of the non-biologically active inhibitory molecules are joined to produce a sequence that encodes a biologically active inhibitory molecule, directly or indirectly. The advantage of this method is to eliminate packaging cells in which a recombination event has occurred before transduction with the recombinant vector.

In a similar fashion, vectors encoding E1 (Vanormondt, et al., *Gene* 11:299, 1980), E2, or other adenoviral gene encoding regions such as E4 (Hogenkamp, et al., *Nucleic Acids Research* 18:2065, 1990), may be incorporated individually or together into adenoviral packaging cells which contain a nucleic acid cassette comprising a nucleic acid sequence encoding a non-biologically active inhibitory molecules so that recombination of one gene with one of the others, or with a different introduced adenoviral vector carrying a nucleic acid sequence encoding a non-biologically active inhibitory molecule will result, directly or indirectly, in a sequence that encodes a biologically active inhibitory molecule. Similarly, other viral vector packaging lines may be constructed with components carrying nucleic acid sequences encoding non-biologically active inhibitory molecules, that, upon undesirable recombination, give rise to nucleic acid sequences encoding, directly or indirectly, biologically active inhibitory molecules.

In another aspect of the invention, a packaging cell line may be generated using a gag/pol vector that contains a nucleic acid cassette comprising a nucleic acid sequence that encodes a non-biologically active inhibitory molecule (e.g., diphtheria toxin) and an env vector that contains a nucleic acid cassette comprising a nucleic acid sequence that encodes a non-biologically active molecule (e.g., diphtheria toxin) in the 5' region of the env vector and a second cassette that encodes a non-biologically active molecule (e.g., HSVTK) in the 3' region of the env vector. Production of replication competent retrovirus from this packaging cell line due to recombination events between the gag/pol and env vectors and between the env and recombinant vectors would be avoided. As described above, the packaging cell can be eliminated in the event of recombination between the gag/pol and env vectors. After transduction with the recombinant vector, a recombination event occurring between the recombinant, gag/pol and env vectors will result in the production of HSVTK or a biologically active inhibitory molecule. Cells that produce HSVTK may be eliminated by administration of acyclovir or ganciclovir, as described above.

Preferred methods and compositions for preserving recombinant viruses are described in U.S. applications entitled *Methods for Preserving Recombinant Retroviruses*, U.S. Ser. No. 08/135,938, now abandoned, and U.S. Ser. No. 08/153,342, now abandoned, herein incorporated by reference.

In another aspect of the invention, pharmaceutical compositions are provided comprising a recombinant viral particle produced using the packaging cells described above in combination with a pharmaceutically acceptable carrier or diluent. Such pharmaceutical compositions may be prepared in liquid or solid form (e.g., lyophilized). The solid form is suspended in a solution prior to parenteral administration. The composition may also be prepared with suitable carriers or diluents for topical, nasal, vaginal, sub-lingual, or rectal administration. Compositions may be further administered by inhalation or injection.

Pharmaceutically acceptable carriers or diluents are nontoxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, lactose, dextrose, glycerol, and ethanol, as well as polypeptides or proteins such as human serum albumin. A particularly preferred composition comprises a vector or recombinant virus in 40 mg/ml mannitol or lactose, 5 mg/ml HSA, 25 mM Tris, pH 7.2, 1 mg/ml arginine and 25 to 75 mM NaCl. This composition is stable at $-70°$ C. for at least six months.

Pharmaceutical compositions of the present invention may additionally include factors which stimulate cell division, and hence uptake and incorporation of a recombinant vector. Such additional factors include, for example, melanocyte stimulating hormone (MSH) for melanomas, or EGF for breast or other epithelial carcinomas.

In various embodiments of the present invention, recombinant viral particles may be administered to a patient by in vivo or ex vivo procedures. In vivo administration routes include, for example, intradermally, intracranially, intraperitoneally, intrathecally, intravenously, subcutaneously, intramuscularly, or even directly into the tumor.

Another aspect of the present invention involves the use of recombinant viral particles or vectors to directly treat a pathogenic agent such as a tumor. For example, the recombinant viral particles or vectors may be directly administered to a tumor by direct injection into several different locations within the body of the tumor, the vector may be injected into a particular artery that supplies blood to the tumor, or the vector may be directly administered to the surface of the tumor (e.g., by application of a topical pharmaceutical composition containing the recombinant vector or a recombinant viral particle). Alternatively, if the tumor has a necrotic center, it may be aspirated and the vector injected directly into the aspirated cavity.

Another aspect of the present invention involves inhibition of tumor growth by ex vivo administration of the recombinant viral particle or vector. Briefly, selected tumor cells are removed and infected with a recombinant vector that directs the expression of one or more anti-tumor agent (s). These infected cells are then administered to an animal to generate an immune response against the modified tumor cells thereby inhibiting the growth of the selected tumor. In one embodiment of the present invention, the recombinant vector in combination with other factors are administered in a suspension to an animal. Briefly, a single cell suspension of the removed tumor cells may be generated by physical disruption or proteolytic digestion. Various factors may be added to this suspension such as MSF (for melanomas) or EGF (for breast carcinomas) to increase cell division in order to enhance uptake, genomic integration and expression of the recombinant vector upon administration to an animal.

Within the context of the present invention it should be understood that the removed cells do not have to be returned to the same animal, but may be used to inhibit the growth of selected tumor cells in another animal. In such a case, it is generally preferable to have histocompatibility matched animals; however, this may not always be required (see, e.g., Yamamoto et al., "*Efficacy of Experimental FIV Vaccines,*" 1st International Conference of FIV Researchers, University of California at Davis, September 1991). Administration directly into a tumor or within the vicinity of a tumor is preferable.

In addition, it should be understood that a variety of cells (target cells) may be used within the context of the present invention, including, for example, human, macaque, equine, bovine, ovine, porcine, canine, feline, rat, mouse, avian, and fish cells.

As noted above, several anti-tumor agents may be administered either concurrently or sequentially in order to inhibit the growth of a selected tumor in accordance with the methods of the present invention. For example, an anti-tumor agent such as γ-IFN may be co-administered or sequentially administered to an animal along with other anti-tumor agents such as IL-2, or IL-12, in order to inhibit or destroy a pathogenic agent. Such therapeutic compositions may be administered directly using a single vector which directs the expression of two or more anti-tumor agents or the anti-tumor agents may be expressed by independent vectors. Alternatively, one anti-tumor agent (e.g., γ-IFN) may be expressed by a vector administered to the animal, while other tumor agents (e.g., IL-2) are administered directly (e.g., intravenously as a pharmaceutical composition).

In a preferred embodiment of the invention, a recombinant vector may be administered to a patient that expresses γ-IFN and IL-2. In such a vector, the first anti-tumor agent may be expressed from an LTR present in the recombinant vector and the other agent may utilize an additional transcriptional promoter located between the LTRs. Alternatively, the second anti-tumor agent may be expressed as a polycistronic mRNA, which may incorporate one or more internal ribosome binding sites. After in vivo gene transfer, the patient's immune system may be activated due to the expression of γ-IFN, thereby resulting in increased infiltration of the dying tumor with inflammatory cells. This infiltration increases immune presentation which further improves the patient's immune response against the tumor.

In another embodiment of the invention, a recombinant vector may be inserted into non-tumorigenic cells, for example, cells derived from skin (e.g., dermal fibroblasts), blood (e.g., peripheral blood leukocytes) or from a particular fraction of cells such as a T-cell subset or stem cells removed from the blood (see WO 91/16116). Recombinant vectors may then be contacted with the removed cells, using any of the above described techniques, followed by administration of the cells to an animal.

The above described methods may additionally comprise the step of depleting fibroblasts or other non-contaminating tumor cells subsequent to removing tumor cells from a warm-blooded animal, and/or the step of inactivating the cells (e.g., by irritation).

As will be understood by one of ordinary skill in the art given the disclosure provided, any of the recombinant vectors described herein may be delivered as a recombinant viral particle or as direct nucleic acid vectors. Such vectors may be delivered using any appropriate physical method of gene transfer discussed above.

The following examples are offered by way of illustration, and provide preferred embodiments of the invention but are not meant to limit the scope thereof. Standard methods for many of the procedures mentioned or described in the following examples, or suitable alternative procedures, are provided in widely recognized manuals of molecular biology such as, for example, Sambrook et al., "Molecular Cloning," Second Edition, Cold Spring Harbor Laboratory Press (1997) and in Ansubel et al., (Eds.), "Current Protocols in Molecular Biology," Greene Associates/Wiley Interscience, New York (1990).

EXAMPLE 1

Selection of a Non-biologically Active Inhibitory Molecule

In constructs, where the diphtheria toxin A-fragment (DT-A) coding region is inserted in a frame to another reading frame, it has to be ensured that the DT-A fragment does not possess any toxic activity. Example 1 describes a method to generate and test DT-A fragments for their toxic acitivity in eukaryotic cells.

A. Construction of a diphtheria toxin fragment A gene cassette in pUC19.

The Sau3A 577 base pair (bp) fragment from plasmid pTH1 (Maxwell et al., *Cancer Res.* 46:4660, 1986), containing the complete coding region of the diphtheria toxin fragment A in which the first two codons, GGCGCT, have been changed to GATCCT, is isolated and ligated into Bam HI digested pUC19 plasmid (Stratagene, San Diego, Calif.). The orientation of the insert is determined by restriction map analysis or sequencing. Plasmid constructs containing the coding region of the diphtheria toxin fragment A in the Hind III to Eco RI orientation are selected. This plasmid construct is designated pDT-Awt.

B. Construction of an expression vector containing a ATG start codon.

To allow expression of coding sequences not containing a start codon, the eukaryotic expression vector must supply an ATG start codon, including the consensus Kozak sequence, for optimal translation initiation. Briefly, the Kozak consensus sequence and the ATG stop codon are prepared as an oligonucleotide cassette. The nucleotide sequence of the Kozak ATG sense strand is:

5'-AGCTTCCACCATGGA-3'   [SEQUENCE ID NO. 1]

The nucleotide sequence of the Kozak ATG anti-sense strand is:

5'-AGCTTCCATGGTGGA-3'   [SEQUENCE ID NO. 2]

These oligonucleotides are annealed and inserted into pSC6 (see U.S. Ser. No. 07/830,417, now abandoned) that has been cleaved with Hind III. The correct orientation is determined by sequencing. This plasmid is designated pSC6/ATG.

C. Construction of a eukaryotic expression vector containing the diphtheria toxin, fragment A coding region.

Plasmid pDT-Awt is cleaved with Bam HI, filled in and then cleaved with Eco RI, releasing a fragment comprising approximately 600 bp of the diphtheria toxin fragment A gene. Plasmid pSC6/ATG is cleaved with Nco I, filled in and then cleaved with Eco RI, and the diphtheria toxin fragment is inserted by ligation. The new plasmid is designated pSC6/ATG/DTAwt.

D. Generation of deletion mutants of the diphtheria toxin fragment A coding region and their insertion into the eucaryotic expression vector pSC6.

To generate deletion mutants, the plasmid pDT-Awt is cleaved with Bam HI, and digested with mung bean nuclease (MBN) to sequentially cleave nucleotides from the 5' terminus of the gene. The reaction is terminated at different time points ranging from 2 to 30 minutes by adjusting the reaction to 25 mM EDTA and heating to 68° C. for 10 minutes. The DNA fragments produced in these reactions are cleaved with Eco RI and the shortened diphtheria toxin fragment A encoding fragments are isolated by agarose gel electrophoresis. The fragments are then inserted into pSC6/ATG. Briefly, the pSC6/ATG plasmid is linearized with Nco I and the ends are filled in using the Klenow fragment of *E. coli* DNA polymerase I. The linearized plasmid is cleaved with Eco RI and the diphtheria toxin DNA fragments are inserted. After ligation, competent *E. coli* are transformed and the DNA sequence of the 5' end of the inserted DT-A fragments is determined.

E. Transient expression to test for toxin activity in eukaryotic cells.

Expression vectors (0.1 to 5 µg of plasmid DNA) containing diphtheria toxin fragment A gene deletion mutants are cotransfected into a suitable eukaryotic cells with a reporter gene expression construct (i.e., 5 µg DNA, for example, a luciferase expression vector pSV2A/L-AD5', De Wet et al., *Mol. Cell. Biol.* 7:725, 1987) into HeLa cells. The cells are transfected using the calcium phosphate precipitation procedure and washed and incubated for 24 hours. The cells are washed, lysed, and assayed for luciferase activity. The resulting luciferase activity measurements are compared to the activity obtained from a plasmid containing the diphtheria toxin fragment A coding region out of frame (e.g., a construct that does not express any active diphtheria toxin fragment A protein). Deletion mutants showing comparable luciferase activity to the frame shift mutant construct contain a biologically inactive diphtheria toxin fragment A protein. Constructs with reduced luciferase activity indicate the presence of biologically active toxin.

EXAMPLE 2

Construction of Nucleic Acid Cassettes

A. Construction of a 5' ribozyme gene fragment/5' splice site nucleic acid cassette.

Figure 3:
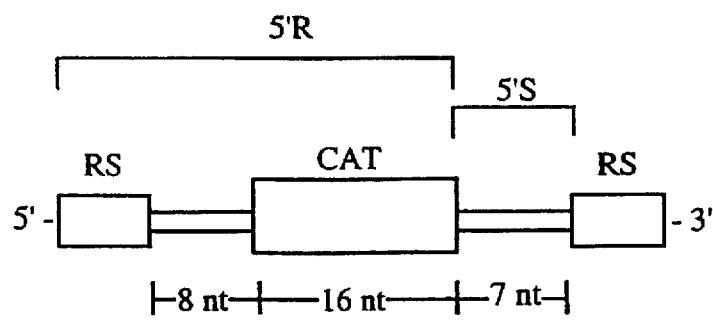
FIG. 3 is a schematic illustration which outlines 5' to 3' the construction of a 5'R/5'S oligonucleotide cassette comprising a 5' restriction endonuclease cleavage site (RS), 8 nucleotides (nt) corresponding to the target sequence that the ribozyme will cleave, 16 nucleotides (nt) of the catalytic cleavage site of the ribozyme (CAT), 7 nucleotides (nt) of the β-globin 5' splice intron sequence (5'S), and 3' restriction endonuclease site (RS).

A double stranded nucleic acid cassette comprising a 5' ribozyme gene fragment (5'R) and a β-globin 5' splice site (5'S) (see FIG. 3) is prepared by DNA synthesis. More specifically, the 5'R/5'S nucleotide sense strand comprises the following nucleotide sequences from 5' to 3' in the order listed: 4 nucleotides, AGCT, representing a portion of the restriction site for Hind III, selected for insertion of the nucleic acid cassette at position 3,250 in plasmid CMVenvAm(Dra) (see WO 92/05266); 8 nucleotides corresponding to the nucleic acid sequence complementary to the 3' portion of the target sequence that the ribozyme will cleave (i.e., position 1,215 to 1,208 of vector KT-1); 16 nucleotides corresponding to the 5' portion of the catalytic cleavage site of the ribozyme; 7 nucleotides corresponding to the first 7 bases of the β-globin 5' splice intron IVS2 sequence (the A in position +4 of the intron IVS 2 sequence has been changed to a C); and 1 adenine nucleotide. This oligonucleotide is designated 5'R/5'S sense and comprises the following sequence:

5'-AGCTTATTCTCACTGATGAGTCC
GTGAGGTGCGTCA-3'   [SEQUENCE ID No. 3]

The 5'R/5'S nucleotide anti-sense strand comprises the following nucleotide sequences from 5' to 3' in the order listed: 5 nucleotides, AGCTT, representing a portion of the restriction site for Hind III, selected for insertion of the nucleic acid cassette at position 3,250 in plasmid CMVenvAm(Dra); 7 nucleotides corresponding to the complementary sequence of the first 7 nucleotides of the human β-globin 5' splice site intron IVS2 sequence; 16 nucleotides corresponding to the complementary sequence of the 5' portion of the catalytic cleavage site of the ribozyme; 8 nucleotides corresponding to the 3' portion of the target sequence to be cleaved by the ribozyme (i.e., position 1,208 to 1,215 in vector KT-1); and 1 adenine nucleotide. This oligonucleotide is designated 5'R/5'S anti-sense and comprises the following nucleotide sequence:

5'-AGCTTGACGCACCTCACGGACT
CATCAGTGAGAATA-3'   [SEQUENCE ID No. 4]

B. Construction of a 3' splice/3' ribozyme gene fragment nucleic acid cassette.

Figure 4:
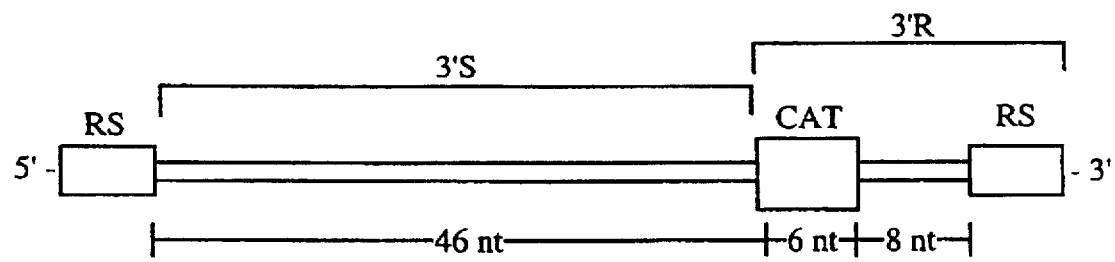
FIG. 4 is a schematic illustration which outlines 5' to 3' the construction of a 3'S/3'R oligonucleotide cassette comprising a 5' restriction endonuclease cleavage site (RS), 46 nucleotides (nt) of the human β-globin 3' splice intron region (3'S), 6 nucleotides of the catalytic cleavage site of the ribozyme (CAT), 8 nucleotides (nt) of the target sequence that the ribozyme will cleave, and a 3' restriction endonuclease site (RS).

A double stranded nucleic acid cassette comprising a 3' β-globin splice site and the remaining portion of the gene sequence of the ribozyme fragment prepared in the 5'R/5'S cassette (see FIG. 4) is synthesized by automated means. The sense strand of the 3'S/3'R nucleic acid cassette comprises the following nucleotide sequences from 5' to 3' in the order listed: 5 nucleotides, CTAGC, representing the restriction site for Nhe I, selected for insertion of the nucleotide cassette (i.e., position 6,616 of vector KT-1); 8 nucleotides corresponding to the 5' portion of the target sequence to be cleaved by the ribozyme; 6 nucleotides corresponding to the 3' portion of the catalytic cleavage site of the ribozyme; 46 nucleotides complementary to the branch point and 3' consensus sequence of the 3' β-globin splice site; and 1 guanine nucleotide representing the restriction site of Nhe I. This oligonucleotide is designated 3'S/3'R antisense and comprises the following nucleotide sequence:

[SEQUENCE ID No. 6]
5'-CTAGCGTATTTGTTTCGTCCTGTGGGAGGAAGATAAGAGGTATG
AACATGATTAGCAAAAGGGCCG-3'

C. Construction of a 5' diphtheria toxin gene fragment/5' splice site env nucleic acid cassette for insertion into plasmid CMVenvAm(Dra).

Figure 5A:
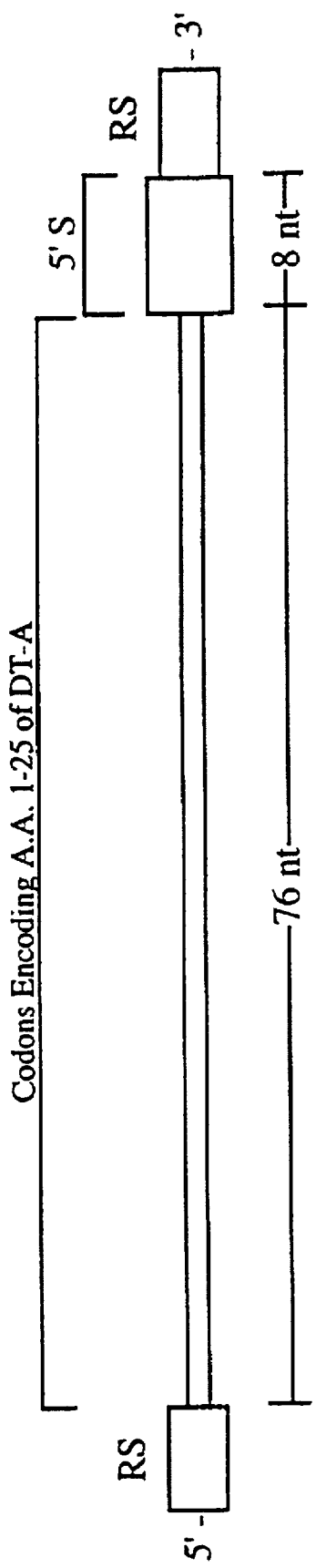
FIG. 5 (Parts A–B) is a schematic illustration which outlines 5' to 3' the construction of: A. 5'DT/5'Senv oligonucleotide cassette comprising a 5' endonuclease restriction site (RS), 76 nucleotides (nt) corresponding to the N-terminal 25 amino acid codons of diphtheria toxin fragment A (DT-A), 9 nucleotides (nt) of the β-globin 5' splice intron sequence (5'S), and a 3' endonuclease restriction site (RS). B. 5'TK/5'S env oligonucleotide cassette comprising a 5' endonuclease restriction site (RS), 45 nucleotides (nt) corresponding to the N-terminal 15 amino acid codons of HSVTK, 9 nucleotides (nt) of the β-globin 5' splice intron sequence (5'S), and a 3' endonuclease restriction site (RS).

The double stranded nucleic acid cassette comprising a 5' diphtheria toxin gene fragment (5'DT) and a β-globin 5' splice site (5'S) (see FIG. 5A) is prepared by DNA synthesis as described above. The sense strand of the 5'DT/5'Senv nucleic acid cassette comprises the following nucleotide sequences from 5' to 3' in the order listed: 5 nucleotides, AGCTT, representing a portion of the restriction site for Hind III, selected for insertion of the nucleic acid cassette at position 3,250 of plasmid CMVenv Am(Dra); 76 nucleotides corresponding to the first 25⅓ amino acid codons of diphtheria toxin; 8 nucleotides corresponding to the first 8 nucleotides of the β-globin 5' splice intron sequence; and 1 adenine nucleotide. This oligonucleotide is designated 5'DT/5'Senv sense and comprises the following nucleotide sequence:

[SEQUENCE ID No. 7]
5'-AGCTTGGCGCTGATGATGTTGTTGATTCTTCTAAATCTTTTGTGA
TGGAAAACTTTTCTTCGTACCACGGGACTAAACCAGGTGAGTCTA-3' tion site for Nhe I, selected for insertion of the nucleotide cassette (i.e., position 6,616 in vector KT-1); 46 nucleotides corresponding to the branch point and 3' intron IVS2 sequence of the human β-globin gene; 6 nucleotides corresponding to the 3' portion of the catalytic cleavage site of the ribozyme; 8 nucleotides complementary to the sequence of the 5' portion of the target sequence that the ribozyme will cleave; and 1 guanine nucleotide representing the restriction site Nhe I. This oligonucleotide is designated 3'S/3'R sense and comprises the following nucleotide sequence:

The anti-sense strand of the 5'DT/5'S nucleic acid cassette comprises the following sequences from 5' to 3' in the order listed: 5 nucleotides, AGCTT, representing a portion of the restriction site for Hind III, selected for insertion of the nucleic acid cassette in plasmid CMVenvAm(Dra); 8 nucleotides complementary to the first 8 bases of the β-globin 5' splice intron sequence; 76 nucleotides complementary to the first 25⅓ amino acid codons of fragment A of the diphtheria toxin gene; and 1 adenine nucleotide. This oligonucleotide is designated 5'DT/5'Senv antisense and comprises the following nucleotide sequence:

[SEQUENCE ID No. 5]
5'-CTAGCGGCCCTTTTGCTAATCATGTTCATACCTCTTATCTTCCTCC
CACAGGACGAAACAAATACG-3'

The anti-sense strand of the 3'S/3'R nucleic acid cassette comprises the following sequences from 5' to 3' in the order

[SEQUENCE ID No. 8]
5'-AGCTTAGACTCACCAGGTTTAGTCCCGTGGTACGAAGAAAAGTTTTC
CATCACAAAAGATTTAGAAGAATCAACAACATCATCAGCGCCA-3'

D. Construction of 5' diphtheria toxin gene fragment/5' splice site gag cassette for insertion into plasmid pSCV10

Figure 6A:
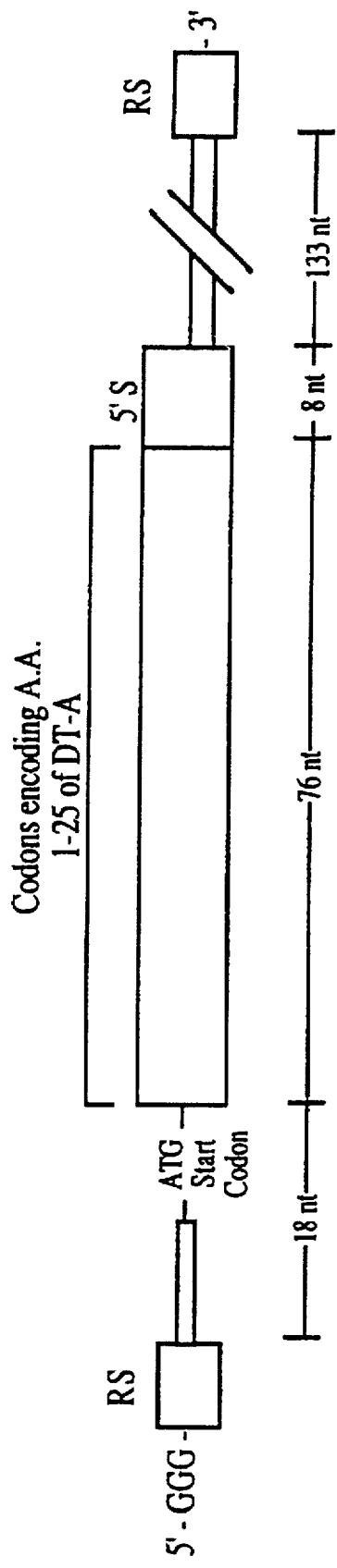
FIG. 6 (Parts A–B) is a schematic illustration which outlines the construction of: A. 5'DT/5'Sgag oligonucleotide cassette comprising, from 5' to 3', 3 guanine nucleotides, a restriction endonuclease site (RS), 18 nucleotides (nt) corresponding to position 762 to 779 of the pSCV10 plasmid of the gag gene, 76 nucleotides (nt) representing the N-terminal 25 amino acid codons of fragment A of the diphtheria toxin gene, 8 nucleotides of the β-globin 5' splice intron IVS2 sequence (5'S), and 133 nucleotides of the gag gene corresponding to position 762–894 of the pSVC10 plasmid and 3' restriction endonuclease site (RS). B. 5'TK/5' gag oligonucleotide cassette comprising, from 5' to 3', 3 guanine nucleotides, a restriction endonuclease site (RS), 16 nucleotides (nt) corresponding to position 761 to 776 of the pSCV10 plasmid of the gag gene, 45 nucleotides (nt) representing the N-terminal 15 amino acid codons of HSVTK, 9 nucleotides of the β-globin 5' splice intron IVS2 sequence (5'S), and 133 nucleotides of the gag gene corresponding to position 762–894 of the pSVC10 plasmid and 3' restriction endonuclease site (RS).

The 5'DT/5'S nucleic acid cassette (see FIG. 6A) is generated by PCR amplification using the oligonucleotide primers DTgag1 and gag2. DTgag1 comprises, in the following order, 3 guanine nucleotides, 6 nucleotides representing the Pst I restriction site sequence CTGCAG, 18 nucleotides located at position 762 to 779 of the pSCV10 plasmid (see WO 92/05266) and including the ATG start codon of the gag gene, 76 nucleotides representing the first 25 amino acid codons of fragment A of the diphtheria toxin gene, 8 nucleotides corresponding to the first 8 nucleotides of the β-globin 5' splice intron IVS2 sequence, and 19 nucleotides located and including the ATG start codon of the gag gene corresponding to position 762–780 of the pSVC10 plasmid. Nucleotide 764 is changed from T to A to generate a TAA stop codon ending the DT-A fragment reading frame. DTgag1 comprises the following nucleotide sequence:

[SEQUENCE ID No. 9]
5'-GGGCTGCAGTATTTGTCTGAAAATATGGGCGCTGATGATGTTGT
TGATTCTTCTAAATCTTTTGTGATGGAAAACTTTTCTTCGTACCAC
GGGACTAAACCAGGTGAGTCTTAATTGTCTGAAAATATGG-3'

Primer gag2 comprises, in the following order, 3 guanine nucleotides, 6 nucleotide representing a Pst I restriction site CTGCAG, and 15 nucleotides complementary to the pSCV10 sequence 894 to 880. gag2 comprises the following nucleotide sequence:

5'-GGGCTGCAGAGCAGAAGGTA
ACCC-3'  [SEQUENCE ID No. 10]

The 5'DT/5'S gag fragment, 241 base pairs in length, is generated by PCR using the primers DTgag1 and gag2, described above, and the plasmid pSCV10 as a template, followed by digestion with restriction enzyme Pst I.

E. Construction of the 3' splice site/3' diphtheria toxin gene/LTR fragment nucleic acid cassette for insertion into plasmid KT-1.

Figure 7A:
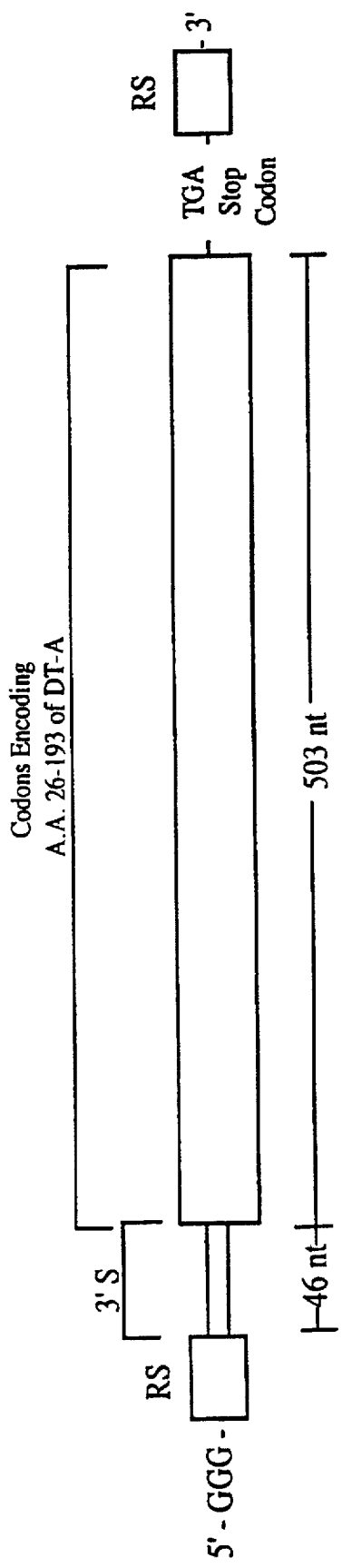
FIG. 7 (Parts A–B) is a schematic illustration which outlines 5' to 3' the construction of: A. the 3'S/3'DT/LTR cassette comprising 3 guanine residues a 5' nuclease restriction site, 46 nucleotides (nt) corresponding to the human β-globin 3' splice intron sequence (3'S), 503 nucleotides (nt) corresponding to amino acid codons 26 to 193 of fragment A of the diphtheria toxin gene (DT) a TGA stop codon and a 3' restriction endonuclease site. B. 3'S/3' TK/LTR cassette comprising 3 guanine residues a 5' nuclease restriction site, 46 nucleotides (nt) corresponding to the human β-globin 3' splice intron sequence, 1083 nucleotides (nt) corresponding to amino acid codons 16 to 376 of HSVTK, a TGA stop codon and a 3' restriction endonuclease site.

The 3' splice site/3' diphtheria toxin gene fragment nucleic acid cassette (3'S/3'DT/LTR; see FIG. 7A) is prepared by polymerase chain reaction (PCR) amplification using oligonucleotide primers DTLTR1 and DTLTR2. The sense strand primer, DTLTR1, comprises the following nucleotide sequences from 5' to 3' in the order listed: 3 guanine residues; 6 nucleotides corresponding to the Nhe I restriction site sequence selected for insertion of the nucleic acid cassette at position 6,616 of KT-1; 46 nucleotides corresponding to the branch point and the 3' intron IVS2 consensus sequence of the human β-globin gene; and 15 nucleotides corresponding to amino acid codons 26 to 30 of fragment A of the diphtheria toxin gene. DTLTR1 comprises the following nucleotide sequence:

[SEQUENCE ID No. 11]
5'-GGGGCTAGCGGCCCTTTTGCTAATCATGTTCATACCTCTTATCTT
CCTCCCACAGGTTATGTAGATTCCA-3'

The antisense strand primer DTLTR2 comprises the following nucleotide sequences from 5' to 3' in the order listed: 3 guanine residues; 6 nucleotides corresponding to the Nhe I restriction site sequence selected for insertion of the nucleic acid cassette at position 6,616 of vector KT-1; 3 nucleotides, TCA, complementary to the stop codon (TGA) and 15 nucleotides complementary to amino acid codons 193-189 of fragment A of the diphtheria toxin gene. DTLTR2 comprises the following nucleotide sequence:

5'-GGGGCTAGCTCATCGCCTGAC
ACGATT-3'  [SEQUENCE ID No. 12]

The 3'S/3'DT/LTR fragment, 558 base pairs in length is generated by PCR using the primers DT LTR1 and DT LTR2 described above and the plasmid pTH1 as a template, followed by digestion with restriction endonuclease Nhe I.

F. Construction of the 3' splice site/3' diphtheria toxin gene fragment env nucleic acid cassette for insertion into plasmid CMVenvAm(Dra).

The 3' splice site/3' diphtheria toxin gene fragment nucleic acid cassette, 3'S/3'DTenv, (see FIG. 7A), is prepared by polymerase chain reaction (PCR) amplification using oligonucleotide primers DTenv1 and DTenv2.

The sense strand primer DTenv1 comprises the following nucleotide sequences from 5' to 3' in the order listed: 3 guanine nucleotides; 6 nucleotides representing the Xma I restriction endonuclease recognition site selected for insertion of the cassette at position 4,222 in plasmid CMVenvAm (Dra); 46 nucleotides corresponding to the branch point and the 3' intron IVS2 sequence of β-globin; gene and 15 nucleotides corresponding to amino acid codons 26 to 30 of fragment A of the diphtheria toxin gene. This sequence is:

[SEQUENCE ID No. 13]
5'-GGGCCCGGGGGCCCTTTTGCTAATCATGTTCATACCTCTTATCT
TCCTCCCACAGGTTATGTAGATTCCA-3'

The antisense strand primer TK env2 comprises the following nucleotide sequences from 5' to 3' in the order listed: 3 guanine nucleotides; 6 nucleotides representing the Xma I restriction endonuclease site for insertion of the cassette at position 4,222 in plasmid CMVenvAm(Dra); 3 nucleotides, TCA, representing the complementary sequence for the stop codon; and 15 nucleotides complementary to the nucleotide sequence encoding amino acids 189 to 193 of fragment A of the diphtheria toxin gene. This sequence is:

5'-GGGCCCGGGTCATCGCCTGAC
ACGATT-3'    [SEQUENCE ID No. 14]

The 3'S/3'DTenv fragment, 558 baseparts in length is generated by PCR using the primus DTenv1 and DTenv2 described above and the plasmid pTH1 as a template, followed by digestion with restriction endonuclease Xma I.

G. Construction of a 5' herpes thymidine kinase (HSVTK) toxin gene fragment/5' splice site env nucleic acid cassette for insertion into plasmid CMVenvAm(Dra).

Figure 5B:
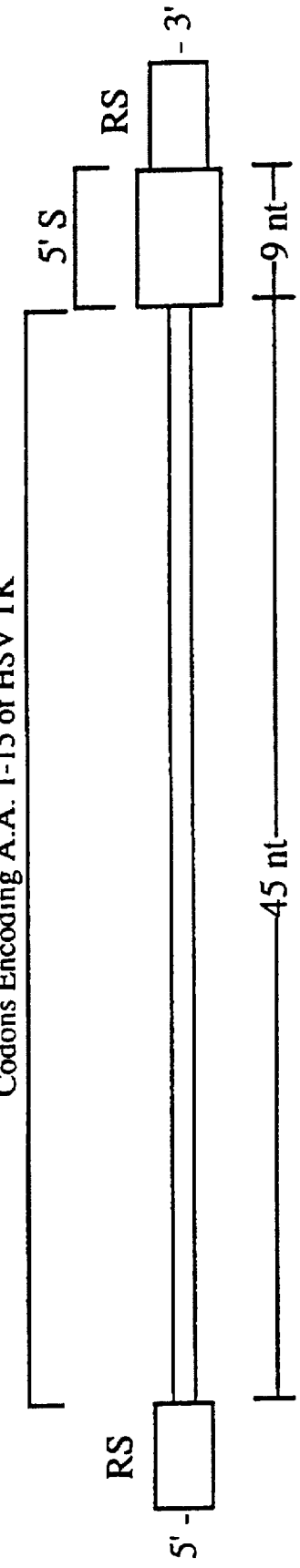

The double stranded nucleic acid cassette comprising a 5' HSVTK gene fragment (5'TK) (see FIG. 5B) and a β-globin 5' splice site (5'S) is prepared by DNA synthesis as described above. The sense strand of the 5'TK/5'Senv nucleic acid cassette comprises the following nucleotide sequences from 5' to 3' in the order listed: 5 nucleotides, AGCTT, representing a portion of the restriction site for Hind III, selected for insertion of the nucleic acid cassette at position 3,250 of plasmid CMVenv Am(Dra); 45 nucleotides corresponding to the first 15 amino acid codons of HSVTK; 9 nucleotides corresponding to the first 9 nucleotides of the β-globin 5' splice intron sequence; and 1 adenine nucleotide. This oligonucleotide is designated 5'TK/5'Senv sense and comprises the following nucleotide sequence:

[SEQUENCE ID No. 15]
5'-AGCTTATGGCTTCGTACCCCTGCCATCAACACGCGTCTGCGT
TCGACCAGGTGAGTCTAA-3'

The anti-sense strand of the 5'TK/5'S nucleic acid cassette comprises the following sequences from 5' to 3' in the order listed: 5 nucleotides, AGCTT, representing a portion of the restriction site for Hind III, selected for insertion of the nucleic acid cassette in plasmid CMVenvAm(Dra); 9 nucleotides complementary to the first 9 bases of the β-globin 5' splice intron sequence; 45 nucleotides complementary to the first 15 amino acid codons of HSVTK gene; and 1 adenine nucleotide. This oligonucleotide is designated 5'DT/5'Senv antisense and comprises the following nucleotide sequence:

[SEQUENCE ID No. 16]
5'-AGCTTTAGACTCACCTGGTCGAACGCAGACGCGTGTTGATGG
CAGGGGTACGAAGCCATA-3'

H. Construction of 5' herpes thymidine kinase gene fragment/5'splice site gag nucleic acid cassette 5'TK/5'S gag for insertion into plasmid pSCV10.

Figure 6B:
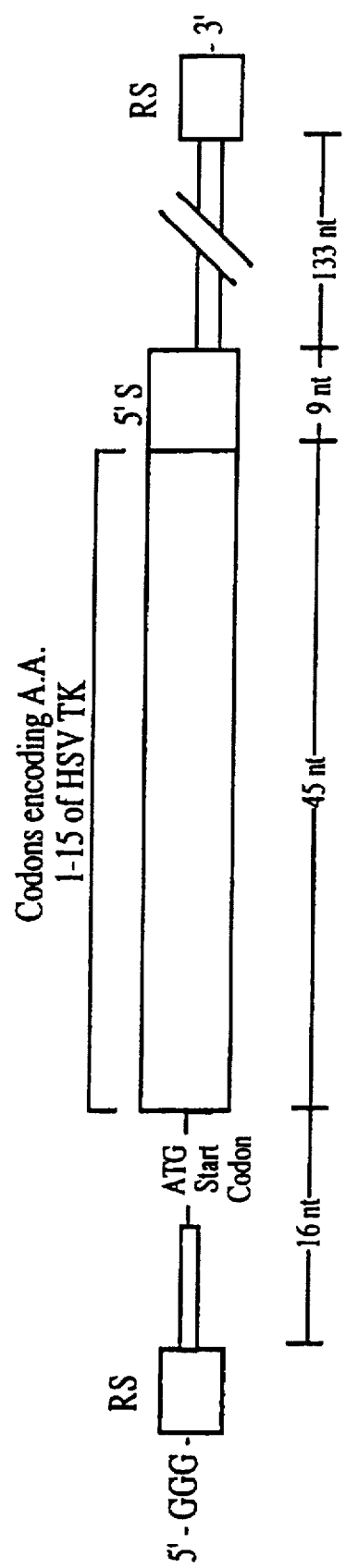

The 5'TK/5'S gag nucleic acid cassette (see FIG. 6B) is generated by PCR amplification using the oligonucleotide primers TKgag1 and gag2. TKgag1 comprises, in the following order, 3 guanine nucleotides, 6 nucleotides representing the Pst I restriction site sequence CTGCAG, nucleotides located at position 761 to 776 of the pSCV10 plasmid (see WO 92/05266) and adjacent to the ATG start codon of the gag gene, 45 nucleotides representing the first 15 amino acid codons of HSVTK, 9 nucleotides corresponding to the first 9 nucleotides of the β-globin 5' splice intron IVS2 sequence, and 19 nucleotides located and including the ATG start codon of the gag gene corresponding to position 762–780 of the pSVC10 plasmid. Nucleotide 764 is changed from T to A to generate a TAA stop codon ending the TK fragment reading frame. TKgag1 comprises the following nucleotide sequence:

[SEQUENCE ID No. 17]
5'-GGGCTGCAGGTATTTGTCTGAAAATATGGCTTCGTACCCCTGC
CATCAACACGCGTCTGCGTTCGACCAGGTGAGTCTATAATTGTCTGA
AAATATGG-3'

Primer gag2 comprises, in the following order, 3 guanine nucleotides, 6 nucleotide representing a Pst I restriction site CTGCAG, and 15 nucleotides complementary to the pSCV10 sequence 894 to 880. gag2 comprises the following nucleotide sequence:

5'-GGGCTGCAGAGCAGAAGGTA
ACCC-3'    [SEQUENCE ID No. 10]

The 5'DT/5'S gag fragment, 209 base pairs in length, is generated by PCR using the primers DTgag1 and gag2, described above, and the plasmid pSCV10 as a template, followed by digestion with restriction enzyme Pst I.

I. Construction of the 3' splice site/3' herpes thymidine kinase gene/LTR fragment nucleic acid cassette for insertion into plasmid KT-1.

The 3' splice site/3' HSVTK gene fragment nucleic acid cassette (3'S/3'TK/LTR) is prepared by polymerase chain reaction (PCR) amplification using oligonucleotide primers TKLTR1 and TKLTR2. The sense strand primer, TKLTR1, comprises the following nucleotide sequences from 5' to 3' in the order listed: 3 guanine amino acid codons 376-372 of the HSVTK gene, 6 nucleotides corresponding to the Nhe I restriction site sequence selected for insertion of the nucleic acid cassette at position 6,616 of KT-1; 46 nucleotides corresponding to the branch point and the 3' intron IVS2 consensus sequence of the human β-globin gene; and 15 nucleotides corresponding to amino acid codons 16 to 20 of HSVTK. TKLTR1 comprises the following nucleotide sequence:

[SEQUENCE ID No. 18]
5'-GGGGCTAGCGGCCCTTTTGCTAATCATGTTCATACCTCTTATCTTC
CTCCCACAGGCTGCGCGTTCTCGC-3'

The antisense strand primer TKLTR2 comprises the following nucleotide sequences from 5' to 3' in the order listed: 3 guanine nucleotides; 6 nucleotides corresponding to the Nhe I restriction site sequence selected for insertion of the nucleic acid cassette at position 6,616 of vector KT-1; 3 nucleotides, TCA, complementary to the stop codon (TGA) and 15 nucleotides complementary to amino acid codons 16 to 20 of the HSVTK gene. This sequence is:

5'-GGGGCTAGCTCAGTTAGCCTC
CCCCAT-3'  [SEQUENCE ID No. 19]

Figure 7B:
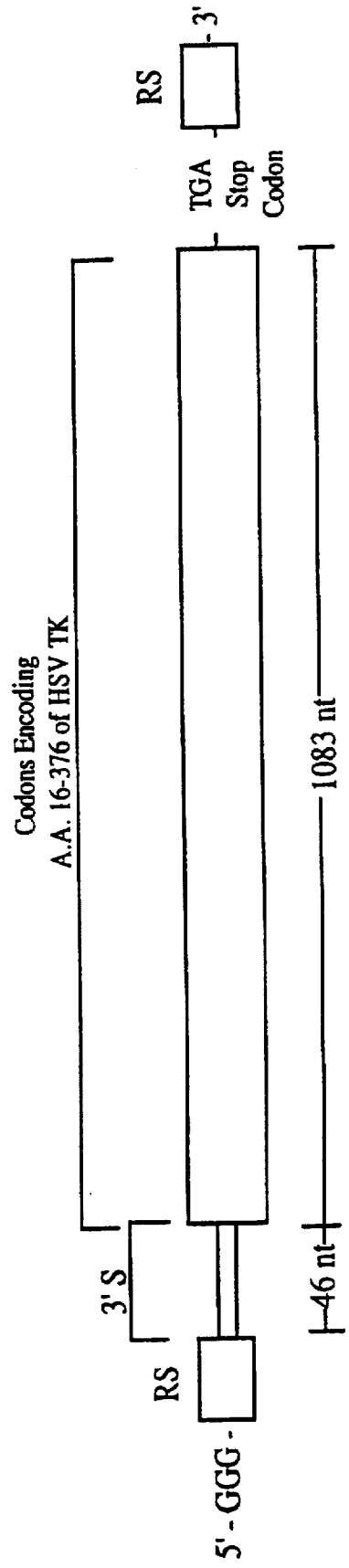

The 3'S/3'TK/LTR fragment, 1,138 base pairs in length is generated by PCR using the primers TKLTR1 and TKLTR2 described above and the plasmid BH-1 as a template, followed by digestion with restriction endonuclease Nhe I (see FIG. 7B).

J. Construction of the 3' splice site/3' herpes thymidine kinase gene fragment nucleic acid cassette for insertion into plasmid CMVenvAm(Dra).

The 3' splice site/3' HSVTK gene fragment nucleic acid cassette, 3'S/3'TK env, is prepared by polymerase chain reaction (PCR) amplification using oligonucleotide primers TKenv1 and TKenv2.

The sense strand primer TKenv1 comprises the following nucleotide sequences from 5' to 3' in the order listed: 3 guanine nucleotides; 6 nucleotides representing the Xma I restriction endonuclease recognition site selected for insertion of the cassette at position 4,222 in plasmid CMVenvAm (Dra); 46 nucleotides corresponding to the branch point and the 3' intron IVS2 sequence of β-globin gene and 15 nucleotides corresponding to amino acid codons 16 to 20 of the HSVTK gene. This sequence is:

[SEQUENCE ID No. 20]
5'-GGGCCCGGGGGCCCTTTTGCTAATCATGTTCATACCTCTTATCT
TCCTCCCACAGGCTGCGCGTTCTCGC-3'

The antisense strand primer TK env2 comprises the following nucleotide sequences from 5' to 3' in the order listed: 3 guanine nucleotides; 6 nucleotides representing the Xma I restriction endonuclease site for insertion of the cassette at position 4,222 in plasmid CMVenvAm(Dra); 3 nucleotides, TCA, representing the complementary sequence for the stop codon; and 15 nucleotides complementary to the nucleotide sequence encoding amino acids 372 to 376 of HSVTK gene. This sequence is:

5'-GGGCCCGGGTCAGTTAGCCTC
CCCCAT-3'  [SEQUENCE ID No. 21]

EXAMPLE 3

Construction of env, gag, and Recombinant Vectors Containing a Nucleic Acid Cassette A. Construction of env vector containing the nucleic acid cassette 5'R/5'S or 5'DT/5'Senv.

Figure 8:
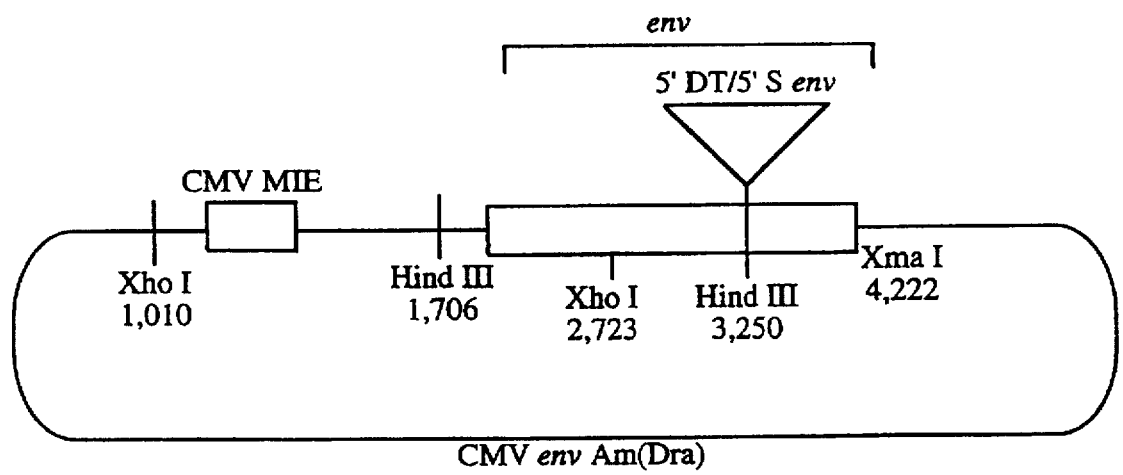
FIG. 8 is a schematic illustration which outlines the construction of CMVenvAm(Dra)5'DT recombinant expression vector, which comprises the 5'DT/5'Senv cassette inserted at the Hind III restriction endonuclease site of the CMVenvAm(Dra) backbone. Xho I and Hind III restriction site positions are indicated as is the CMV(MIE) promoter.

CMVenvAm(Dra)(see U.S. Ser. No. 07/586,603, now abandoned) is cleaved with Xho I to isolate a 1,713 base pair fragment containing the CMV promoter and the 5' end of the amphotropic env gene. The remaining plasmid comprising 4,785 base pairs is then religated using T4 DNA ligase (Promega, Madison, Wis.). This plasmid is designated ΔenvAm(Dra). ΔenvAm(Dra) is then linearized with Hind III and dephosphorylated using calf intestine alkaline phosphatase (CIAP). A 5'R/5'S or 5'DT/5'Senv cassette are phosphorylated and ligated to the linearized, dephosphorylated ΔenvAm(Dra) plasmid. The correct orientation of the cassette in the resultant plasmid is determined by sequencing or restriction map analysis. One clone for each cassette, designated ΔenvAm(Dra)5'R/5'S and ΔenvAm(Dra)5'DT/5'S, respectively, is retained. The new plasmids are linearized with Xho I and dephosphorylated with CIAP and religated with the 1,713 base pair Xho I fragment isolated above. The correct orientation of the plasmid is determined by digestion with restriction endonuclease Eco RI. The new plasmids with the correct orientation are designated CMVenvAm (Dra)5'R and CMVenvAm(Dra)5'DT (see FIG. 8).

B. Construction of a gag/pol expression vector containing the 5'DT/5'S gag nucleic acid cassette.

Figure 11:
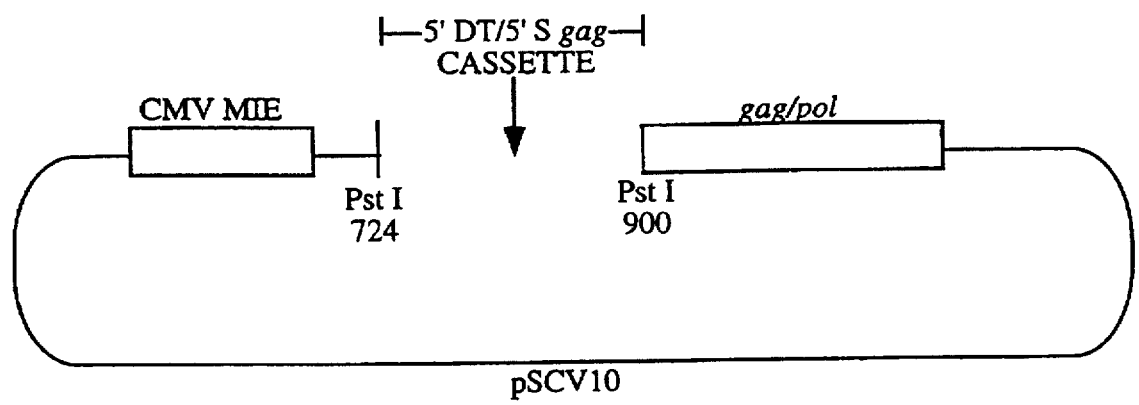
FIG. 11 is a schematic illustration which outlines the construction of the pSCV10/5'DT recombinant expression vector comprising the 5'DT/5'Sgag cassette replacing the Pst I (position 724)/Pst I (position 900) fragment of plasmid pSCV10 before the gag/pol gene and after the CMV (MIE) promoter.

The 5'DT/5'S gag fragment, described from Example 2D, is inserted into pSCV10 to replace the original gag-containing Pst I fragment at position 724 to 900 of the plasmid. Plasmid pSCV10 is cleaved with Pst I and dephosphorylated using CIAP. A stop codon is inserted after the splice site to prevent production of a DT fragment/gag hybrid protein. It is expected that the ribosome will start translation at the gag ATG start codon because ribosomes are known to skip short reading frames such as the DT reading frame present in the gag cassettes. Alternatively, an IRES sequence can be inserted between the gag cassette and the gag reading frame. The dephosphorylated plasmid and the 5'DT/5'S gag nucleic acid cassette are ligated and used to transform competent DH5 E. coli cells. Plasmid DNA from transformed E. coli colonies is prepared and screened for the correct orientation of the 5'DT/5'S gag nucleic acid cassette. Sequence analysis is performed on putative clones to confirm the correct sequence. One sequence verified clone, designated pSCV10/5'DT is retained (see FIG. 11).

C. Construction of an env expression vector containing the 3'S/3'DTenv nucleic acid cassette.

Figure 9:
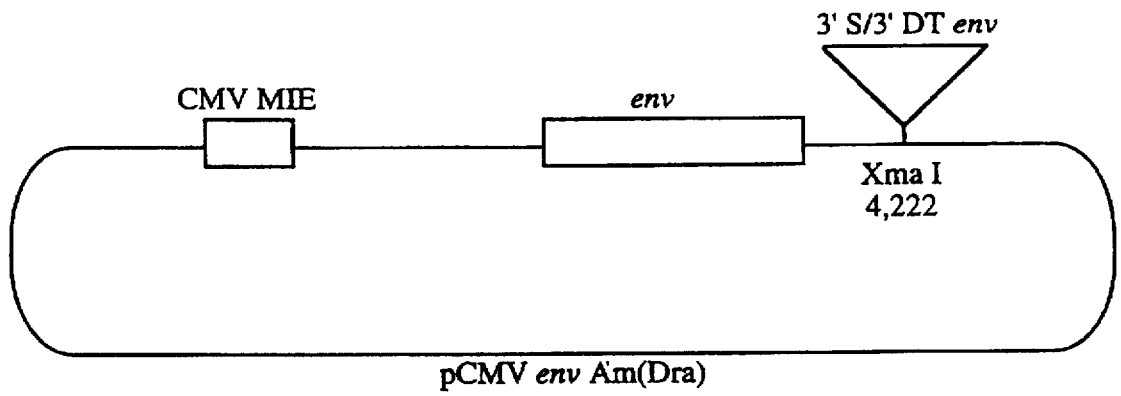
FIG. 9 is a schematic illustration which outlines the construction of the CMVenvAm(Dra)3'DT recombinant expression vector, which comprises the 3'S/3'DTenv cassette inserted at the Xma I site of plasmid CMVenvAm(Dra).

Plasmid CMVenvAm(Dra) is linearized with Xma I and dephosphorylated using CIAP. The dephosphorylated plasmid and the 3'S/3'DTenv nucleic acid cassette are ligated and used to transform competent DH5 E. coli cells. Plasmid DNA from transformed E. coli colonies is prepared and screened for the correct orientation of the 3'S/3'DTenv nucleic acid cassette. Sequence analysis is performed on the plasmid to confirm the correct sequence. This product is designated CMVenvAm(Dra)3'DT (see FIG. 9).

D. Construction of a retroviral vector containing a diphtheria toxin gene fragment/splice site nucleic acid cassette or a ribozyme gene fragment/splice site nucleic acid cassette.

Figure 10:
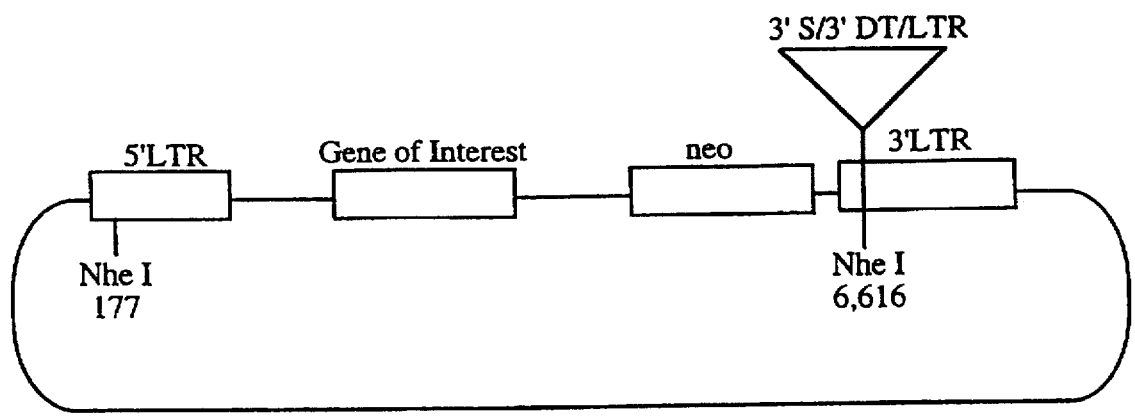
FIG. 10 is a schematic illustration which outlines the construction of the KT-1/3'DT recombinant expression vector comprising the 3'S/3'DT/LTR cassette inserted at the Nhe I restriction endonuclease site within the 3'LTR region of the retrovector KT-1. Also indicated are relative locations of the neomycin resistance gene (neo) and a gene of interest (GOI) and 5' and 3'LTRs.

Construction of the KT-1 recombinant retroviral vector has been previously described in patent application WO 91/02805, herein incorporated by reference. The 3'S/3'R or 3'S/3'DT/LTR nucleic acid cassette, described in Example 2B and Example 2E, respectively, is inserted into the KT-1 retroviral vector at the Nhe I restriction site located 30 nucleotides downstream from the 5' end of the 3' LTR by independently digesting the KT-1 retroviral vector and the 3'S/3'R or 3'S/3'DT/LTR nucleic acid cassette with Nhe I. The linearized, partially digested KT-1 retroviral vector is isolated by gel electrophoresis and dephosphorylated with CIAP. The Nhe I digested 3'S/3'R or 3'S/3'DT/LTR nucleic acid cassette is then ligated with the linearized KT-1 retroviral vector. The ligation products are then used to transform competent DH5 *E. coli* cells. The correct insertion site and orientation of the inserted cassette is confirmed by sequence analysis. The retroviral vectors produced are designated KT-1/3'R (no figure) and KT-1/3'DT (see FIG. 10), respectively.

E. Construction of env vector containing the nucleic acid cassette 5'R/5'S 5'DT/5'Senv, or 5'TK/5'Senv CMVenvAm(Dra)(see U.S. Ser. No. 07/586,603, now abandoned) is cleaved with Xho I to isolate a 1,713 base pair fragment containing the CMV promoter and the 5' end of the amphotropic env gene. The remaining plasmid comprising 4,785 base pairs is then religated using T4 DNA ligase (Promega, Madison, Wis.). This plasmid is designated ΔenvAm(Dra). ΔenvAm(Dra) is then linearized with Hind III and dephosphorylated using calf intestine alkaline phosphatase (CIAP). A 5'R/5'S, 5'DT/5'Senv, or 5'TK/5'Senv cassette are phosphorylated and ligated to the linearized, dephosphorylated ΔenvAm(Dra) plasmid. The correct orientation of the cassette in the resultant plasmid is determined by sequencing or restriction analysis. One clone for each cassette, designated ΔenvAm(Dra)5'R/5'S, ΔenvAm(Dra)5'DT/5'S, ΔenvAm(Dra)5'TK/5'S and ΔenvAm(Dra)5'TK/5'S, respectively, is retained. The new plasmids are linearized with Xho I and dephosphorylated with CIAP and religated with the 1,713 base pair Xho I fragment isolated above. The correct orientation of the plasmid is determined by digestion with restriction endonuclease Eco RI. The new plasmids with the correct orientation are designated CMVenvAm(Dra)5'R, CMVenvAm(Dra)5'DT, and CMVenvAm(Dra)5'TK.

F. Construction of a gag/pol expression vector containing the 5'DT/5'S gag or the 5'TK/5'S gag nucleic acid cassette.

The 5'DT/5'S gag or the 5'TK/5'Sgag fragment, described from Example 2D, is inserted into pSCV10 to replace the original gag-containing Pst I fragment at position 724 to 900 of the plasmid. Plasmid pSCV10 is cleaved with Pst I and dephosphorylated using CIAP. A stop codon is inserted after the splice site to prevent production of a DT fragment/gag hybrid protein. It is expected that the ribosome will start translation at the gag ATG start codon because ribosomes are known to skip short reading frames such as the DT reading frame present in the gag cassettes. Alternatively, an IRES sequence can be inserted between the gag cassette and the gag reading frame. The dephosphorylated plasmid and the 5'DT/5'S gag (or 5'TK/5'Sgag) nucleic acid cassette are ligated and used to transform competent DH5 *E. coli* cells. Plasmid DNA from transformed *E. coli* colonies is prepared and screened for the correct orientation of the 5'DT/5'S gag (or 5'TK/5'Sgag) nucleic acid cassette. Sequence analysis is performed on putative clones to confirm the correct sequence. One sequence verified clone, designated pSCV10/5'DT or pSCV10/5'TK, respectively is retained.

G. Construction of an env expression vector containing the 3'S/3'DTenv (or 3'S/3'TKenv)nucleic acid cassette.

Plasmid CMVenvAm(Dra) is linearized with Xma I and dephosphorylated using CIAP. The dephosphorylated plasmid and the 3'S/3'DTenv (or 3'S/3'TKenv) nucleic acid cassette are ligated and used to transform competent DH5 *E. coli* cells. Plasmid DNA from transformed *E. coli* colonies is prepared and screened for the correct orientation of the 3'S/3'DTenv (or the 3'S/3'TKenv) nucleic acid cassette. Sequence analysis is performed on the plasmid to confirm the correct sequence. This product is designated CMVenvAm(Dra)3'DT (or CMVenvAm(Dra)3'TK).

H. Construction of a retroviral vector containing a diphtheria toxin gene fragment/splice site or a herpes thymidine kinase gene fragment splice site nucleic acid cassette.

Construction of the KT-1 recombinant retroviral vector has been previously described in patent application WO 91/02805, herein incorporated by reference. The 3'S/3'R, 3'S/3'DT/LTR or 3'S/3'TK/LTR nucleic acid cassette, described in Examples 2B, 2E and 2I, respectively, is inserted into the KT-1 retroviral vector at the Nhe I restriction site located 30 nucleotides downstream from the 5' end of the 3' LTR by independently digesting the KT-1 retroviral vector and the 3'S/3'R, 3'S/3'DT/LTR or 3'S/3'TK/LTR nucleic acid cassette with Nhe I. The linearized, partially digested KT-1 retroviral vector is isolated by gel electrophoresis and dephosphorylated with CIAP. The Nhe I digested 3'S/3'R, 3'S/3'DT/LTR or 3'S/3'TK/LTR nucleic acid cassette is then ligated with the linearized KT-1 retroviral vector. The ligation products are then used to transform competent DH5 *E. coli* cells. The correct insertion site and orientation of the inserted cassette is confirmed by sequence analysis. The retroviral vectors produced are designated KT-1/3'R, KT-1/3'DT, and KT-1/3'TK.

EXAMPLE 4

Generation of Packaging Cells

A. Transformation of a cell line with gag/pol vector.

D17 cells (ATCC No. CCL 183) are co-transfected with 1 µg of the methotrexate resistance vector, pFR400 (Graham and Van der Eb, *Virology* 52:456, 1973), and 10 µg of pSCV10/5'DT vector by calcium phosphate co-precipitation. Transformed cells are selected in the presence of dipyrimidol and methotrexate (Vinh et al., *J. Pharm. Exp. Therap.* 267:989, 1993). After selection for transformed cells, individual drug resistant cell colonies are expanded and analyzed for intracellular expression of MoMLV p30gag by Western blot using anti-p30gag antibodies. Clones producing the highest level of p30gag protein are selected for transfection with the env vectors. The cell clones selected are designated D17/pSCV10/5'DT.

B. Transformation of D17/gag/pol cell clones with env vector.

The D17gag/pol clone D17/pSCV10 and D17/pSCV10/5'DT are each co-transfected with 1 µg of the phleomycin resistance vector, pUT507 (Mulsant et al., *Somat. Cell Mol. Genet.* 14:243, 1988), and 10 µg of the amphotropic env vector CMVenvAm(Dra), CMVenvAm(Dra)/5'DT or CMVenvAm(Dra)/3'DT. After selection for transfected cells in the presence of phleomycin, individual drug resistant cell colonies are expanded and analyzed for intracellular expression of gp70env protein by Western blot using anti-gp70env. Clones producing the highest levels of p30gag and gp70env protein are selected to generate vector producing cell lines. These packaging cells are designated D17/pSCV10/CMVenvAm(Dra), D17/pSCV10/CMVenvAm(Dra)5'DT, D17/pSCV10/CMVenvAm(Dra)/3'DT, D17/pSCV10/5'DT/CMVenvAm(Dra), and D17/pSCV10/5'DT/CMVenvAm(Dra)3'DT, respectively. The clone D17/pSCV10/5'DT/pCMVenvAm(Dra)/5'DT is not selected because it contains two 5'DT gene fragments.

C. Production of a recombinant retroviral vector from a D17 PCL.

293 2-3 cells, derived from the 293 cell line (ATCC No. CRL 1573), are transfected with the VSV G protein expression vector and recombinant vector to produce VSV G protein pseudo typed vector as follows: 10 µg of KT-1 recombinant retroviral vector is co-transfected with 10 µg of the VSV G protein expression vector MLP G (see U.S. Ser. No. 07/586,603, now abandoned) into 293 2-3 cells. The resulting transfected cells produce VSV G pseudo typed recombinant vector, transiently and after 2 days, cell free supernatants are added to D17 based packaging cell lines described in Example 4B. Vector infected cells are obtained by selection with G418. After selection and cell clone expansion, cell free supernatants are collected from confluent monolayers and titered onto NIH 3T3 TK⁻ cells (ATTC No. CCL 163). Resulting high titer clones derived from the transduced cells are selected with G418 (packaging cell lines (PCLs)).

EXAMPLE 5

Vector Integrity and Expression in DA and D17 PCLs

KT-1/3'DT and KT-1 vectors are introduced into the D17/pSCV10/CMVenvAm(Dra)/5'DT and DA packaging cell lines by infection as VSV G protein pseudo-typed vectors. For example, a VSV G protein pseudo-typed vector is generated by co-transfecting 10 µg of KT-1/3'DT plasmid or KT-1 plasmid and 10 µg of VSV G protein expression vector MLP G into 293 2-3 cells. The resulting pseudo-typed recombinant retrovirus vector is produced transiently in the co-transfected cells. Approximately 2 days after transfection, the cell free supernatant is added to the D17/pSCV10/CMVenvAm(Dra)/5'DT and DA packaging cell lines. The cells infected with the pseudo-typed vectors are grown under G418 selection for two weeks. After G418 selection, the supernatant is tested for vector titer on NIH3T3 TK-cells. These clones are designated D17/5'DT/KT-1/3'DT, DA/KT-1/3'DT, D17/5'DT/KT-1, and DA/KT-1.

HT1080 cells (ATCC No. CCL 121) are transduced using cell free supernatants from D17/5'DT/KT-1/3'DT, DA/KT-1/3'DT, D17/5'DT/KT-1, and DA/KT-1 vector producing cell pools at a multiplicity of infection greater than one. The transduced cells are harvested after 2 days of growth under G418 selection. Transient expression of HIV-I env in these cells is analyzed by Western blot using anti-gp70 antibodies.

In addition, individual drug resistant cell colonies are expanded and analyzed for stability of integrated provector sequences by Southern blot analysis. Specifically, genomic DNA is isolated from individual clones and cleaved either with Xba I alone or with Xba and Sal I in a double digest. The double digest releases a 600 bp Xba I/Sal I fragment of the KT-1 provector, or 1,158 bp fragment of KT-1/3'DT provirus. The Southern blot is analyzed using the Xba I/Sal I 600 bp fragment of KT-1 as a probe labeled with ³²P. The absence of bands comprising DNA sequences less than 1,158 bp indicates that KT-1/3'DT vector production is stable and that provector DNA has integrated into the cellular chromosomes.

EXAMPLE 6

Test System for the Generation of Replication Competent Retrovirus

A vector is constructed that contains the MoMLV genes gag, pol, and amphotropic env under the control of the MoMLV 5'LTR (see U.S. Ser. No. 07/395,932, now abandoned). When this vector and a MoMLV-based retroviral vector, e.g., KT-1, are present in a producer cell, only one recombination event is necessary to generate a replication competent retrovirus. Consequently, a vector producing cell containing this gag/pol/env expression construct and KT-1 retrovector generates replication competent retrovirus with higher frequency.

A. Construction of the pLTRgpe gag/pol/env vector.

The vector pLTRgpe gag/pol/env is constructed by ligation of fragments from pAM, pCMVenvAm(Dra), and pBluescript II SK⁺ (Stratagene, San Diego, Calif.). The fragments to be ligated are the Eco RI (upstream of the Cla I site 591 nucleotides 5' of the R region of 5'LTR)/Eco RI (positioned 1,415 nucleotides upstream of the 3' LTR of 4070A MoMLV) 6,974 bp fragment from pAM, the Eco RI (nucleotide position 1,761)/Sac II (nucleotide position 3,629) 1,868 bp fragment from CMVenvAm(Dra) (which contains an internal Eco RI site; as a result, the fragment is obtained by performing a partial Eco RI digest followed by a complete Sac II digest), and the Eco RI (nucleotide position 701)/Sac II (nucleotide position 751) 2,911 bp fragment from pBluescript II SK⁺. The correct orientation of the construct is confirmed by restriction digests. This vector is designated pLTRgpe.

B. Construction of the pLTRgpe/DT1 gag/pol/env diphtheria toxin vector.

The vector is constructed by ligation of fragments from pAM, CMVenvAm(Dra)/5'DT, and pBluescript II SK⁺. The fragments to be ligated are the Eco RI (upstream of the Cla I site 591 nucleotides 5' of the R region of 5'LTR)/Eco RI (positioned 1415 nucleotides upstream of the 3'LTR of 4070A MoMLV) 6,974 bp fragment from pAM, the Eco RI (nucleotide position 1,761)/Sac II (nucleotide position 3,719) 1,958 bp fragment from CMVenvAm(Dra)/5'DT (contains an internal Eco RI site; the fragment is obtained by partial Eco RI digest followed by a complete Sac II digest), and the Eco RI (nucleotide position 701)/Sac II (nucleotide position 751) 2,911 bp fragment from pBluescript II SK⁺. The correct orientation of the construct is confirmed by restriction digests. This vector is designated pLTRgpe/5'DT.

C. Generation of stable packaging cell lines.

Approximately 10 µg each of the expression vectors pLTRgpe and pLTRgpe/5'DT are co-transfected into D17 cells together with 1 µg of the phleomycin resistance vector, pUT507 (Mulsant et al., *Somat. Cell Mol. Genet.* 14:243, 1988). Transfected cells are selected for phleomycin resistance and individual drug resistant cell colonies are expanded and analyzed for p30gag and gp70env expression by Western blot. Clones expressing high levels of these proteins are selected for transduction experiments with KT-1 and KT-1/3'DT. The selected clones are designated D 17/LTRgpe and D 17/LTRgpe/5'DT.

D. Transduction of packaging cell lines D17/LTRgpe and D17/LTRgpe/5'DT with KT-1 and KT-1/3'DT.

Packaging cell lines D17/LTRgpe and D17/LTRgpe/5'DT are transduced with VSV G protein pseudo-typed KT-1 and KT-1/3'DT vectors. Supernatants are collected after 3, 7, and 14 days and tested for the presence of replication competent retrovirus using the MdH marker rescue assay. More specifically, the collected supernatants are filtered through 0.45 mm cellulose acetate filters and added to 6 cm wells containing 2×10⁵ MdH cells that have been treated with 4 µg/ml polybrene. Mdh cells are derived from *Mus dunni* cells (Lander et al., *J. Vir.* 52:695, 1994) and contain LHL (a hygromycin resistance marker non-replication competent retroviral vector, Palmer et al., *PNAS* 84:1055, 1987). After 24 hours, the medium is replaced with fresh media. Following a 48 hour incubation period, cell supernatants are collected, filtered, and added to 6 cm wells containing 1×10⁵ *Mus dunni* cells that have been treated with 4 µg/ml polybrene. Following a 24 hour incubation, the *Mus dunni* cells are selected for hygromycin resistance. The presence of hygromycin resistant cells indicates generation of RCR. Specifically, D17/LTRgpe transformed with KT-1 or KT-1/3'DT and D17/LTRgpe/5'DT transformed with KT-1 produce RCR. No RCR is produced from the packaging cell line D17/LTRgpe/5'DT transformed with KT-1/3'DT.

While the present invention has been described above both generally and in terms of preferred embodiments, it is understood that variations and modification will occur to those skilled in the art in light of the description, supra.

Therefore, it is intended that the appended claims cover all such variations coming within the scope of the invention as claimed.

Additionally, the publications and other materials cited to illuminate the background of the invention, and in particular cases to provide additional details concerning its practice are herein incorporated by reference.

---

We claim:

1. A vector for directing the expression of a retroviral structural polypeptide, the vector comprising a promoter operably associated with a structural gene construct and a polyadenylation signal, the structural gene construct comprising a nucleic acid molecule coding for the retroviral structural polypeptide and a non-biologically active inhibitory molecule, wherein the vector inhibits production of replication competent retrovirus resulting from recombination events in retroviral packaging or producer cells.

2. The vector according to claim 1 wherein the retroviral structural polypeptide encoded by the structural gene construct is selected from the group consisting of retroviral env and gag/pol.

3. The vector according to claim 1 wherein the non-biologically active inhibitory molecule is a toxin selected from the group consisting of tetanus, ricin, and diphtheria toxin.

4. The vector according to claim 1 wherein the non-biologically active inhibitory molecule is a ribozyme.

5. The vector according to claim 1 wherein the non-biologically active inhibitory molecule is a prodrug activating enzyme.

6. The vector according to claim 1 wherein the nucleic acid molecule of the structural gene construct further comprises a splice site adjacent to be nucleic acid molecule.

7. A recombinant retroviral vector comprising;
a) an LTR;
b) a packaging signal;
c) a tRNA binding site;
d) a gene of interest; and
e) a nucleic acid cassette comprising a nucleic acid molecule encoding a non-biologically active inhibitory molecule which results in a nucleic acid molecule encoding a biologically active inhibitory molecule upon recombination with the vector according to claim 1.

8. The packaging cell comprising the vector according to claim 1.

9. The vector according to claim 2 wherein the promoter is selected from the group consisting of an RSV promoter, adenovirus MLP, an SV40 promoter, and CMV MIE.

10. The vector according to claim 2 wherein the retroviral structural polypeptide is env derived from a retrovirus selected from the group consisting of MoMLV, 4070A, HTLV-I, HTLV-II, HIV, MPMV, SRV-I, HFV, MFV, SIV, GALV, BLV, FeLV, and FIV.

11. The vector according to claim 2 wherein the retroviral structural polypeptide is env selected from an amphotropic, polytropic or xenotropic retrovirus.

12. The vector according to claim 2 wherein gag/pol is derived from a MoMLV retrovirus.

13. The vector according to claim 11 wherein env is derived from a murine retrovirus.

14. The vector according to claim 5 wherein the non-biologically active inhibitory molecule is the prodrug activating enzyme HSVTK.

15. The recombinant vector according to claim 7 which further comprises a selectable marker.

16. The recombinant vector according to claim 7 wherein the nucleic acid molecule encoding the non-biologically active inhibitory molecule is contained in an LTR.

17. A producer cell comprising at least one vector encoding retroviral gag/pol and env polypeptides and the recombinant retroviral vector according to claim 7.

18. The packaging cell according to claim 8 comprising a vector encoding a retroviral gag/pol polypeptide.

19. The packaging cell line according to claim 8 wherein said packaging cell is generated from D17 or HT1080 cells.

20. The packaging cell according to claim 18 further comprising another vector encoding a retroviral env polypeptide.

21. The retroviral packaging cell according to claim 18 further comprising another vector encoding a VSV G polypeptide.

22. A retroviral particle comprising a recombinant retroviral vector made by the producer cell according to claim 17.

23. A target cell transduced with the retroviral particle according to claim 22.

24. The target cell according to claim 23 that is an animal cell.

25. The target cell according to claim 24 wherein the animal cell is a human cell.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:1:

AGCTTCCACC ATGGA 15

( 2 ) INFORMATION FOR SEQ ID NO:2:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:2:

AGCTTCCATG GTGGA 15

( 2 ) INFORMATION FOR SEQ ID NO:3:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

AGCTTATTCT CACTGATGAG TCCGTGAGGT GCGTCA 36

( 2 ) INFORMATION FOR SEQ ID NO:4:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:4:

AGCTTGACGC ACCTCACGGA CTCATCAGTG AGAATA 36

( 2 ) INFORMATION FOR SEQ ID NO:5:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

CTAGCGGCCC TTTTGCTAAT CATGTTCATA CCTCTTATCT 40

TCCTCCCACA GGACGAAACA AATACG 66

(2) INFORMATION FOR SEQ ID NO:6:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

CTAGCGTATT TGTTTCGTCC TGTGGGAGGA AGATAAGAGG 40

TATGAACATG ATTAGCAAAA GGGCCG 66

(2) INFORMATION FOR SEQ ID NO:7:

(i) SEQUENCE CHARACTERISTICS:
(A) LENGTH: 90 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

AGCTTGGCGC TGATGATGTT GTTGATTCTT CTAAATCTTT 40

TGTGATGGAA AACTTTTCTT CGTACCACGG GACTAAACCA 80

GGTGAGTCTA 90

(2) INFORMATION FOR SEQ ID NO:8:

(i) SEQUENCE CHARACTERISTICS:
(A) LENGTH: 90 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

AGCTTAGACT CACCAGGTTT AGTCCCGTGG TACGAAGAAA 40

AGTTTTCCAT CACAAAAGAT TTAGAAGAAT CAACAACATC 80

ATCAGCGCCA 90

(2) INFORMATION FOR SEQ ID NO:9:

(i) SEQUENCE CHARACTERISTICS:
(A) LENGTH: 130 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:9:

GGGCTGCAGT ATTTGTCTGA AAATATGGGC GCTGATGATG 40

TTGTTGATTC TTCTAAATCT TTTGTGATGG AAAACTTTTC 80

TTCGTACCAC GGGACTAAAC CAGGTGAGTC TTAATTGTCT 120

GAAAATATGG 130

( 2 ) INFORMATION FOR SEQ ID NO:10:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:10:

GGGCTGCAGA GCAGAAGGTA ACCC 24

( 2 ) INFORMATION FOR SEQ ID NO:11:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:11:

GGGGCTAGCG GCCCTTTTGC TAATCATGTT CATACCTCTT 40

ATCTTCCTCC CACAGGTTAT GTAGATTCCA 70

( 2 ) INFORMATION FOR SEQ ID NO:12:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:12:

GGGGCTAGCT CATCGCCTGA CACGATT 27

( 2 ) INFORMATION FOR SEQ ID NO:13:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:13:

GGGCCCGGGG GCCCTTTTGC TAATCATGTT CATACCTCTT 40

ATCTTCCTCC CACAGGTTAT GTAGATTCCA 70

( 2 ) INFORMATION FOR SEQ ID NO:14:

( i ) SEQUENCE CHARACTERISTICS:
    ( A ) LENGTH: 27 base pairs
    ( B ) TYPE: nucleic acid ( C ) STRANDEDNESS: single
            ( D ) TOPOLOGY: linear ( i i ) MOLECULE TYPE: cDNA ( x i ) SEQUENCE DESCRIPTION: SEQ ID NO:14:

GGGCCCGGGT CATCGCCTGA CACGATT 27

( 2 ) INFORMATION FOR SEQ ID NO:15:

( i ) SEQUENCE CHARACTERISTICS:
            ( A ) LENGTH: 60 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:15:

AGCTTATGGC TTCGTACCCC TGCCATCAAC ACGCGTCTGC 40

GTTCGACCAG GTGAGTCTAA 60

( 2 ) INFORMATION FOR SEQ ID NO:16:

( i ) SEQUENCE CHARACTERISTICS:
            ( A ) LENGTH: 60 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:16:

AGCTTTAGAC TCACCTGGTC CAACGCAGAC GCGTGTTGAT 40

GGCAGGGGTA CGAAGCCATA 60

( 2 ) INFORMATION FOR SEQ ID NO:17:

( i ) SEQUENCE CHARACTERISTICS:
            ( A ) LENGTH: 97 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:17:

GGGCTGCAGG TATTTGTCTG AAAATATGGC TTCGTACCCC 40

TGCCATCAAC ACGCGTCTGC GTTCGACCAG TGAGTCTATA 80

ATTGTCTGAA AATATGG 97

( 2 ) INFORMATION FOR SEQ ID NO:18:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:18:

GGGCTGCAGA GCAGAAGGTA ACCC 24

( 2 ) INFORMATION FOR SEQ ID NO:19:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:19:

GGGGCTAGCT CAGTTAGCCT CCCCCAT 27

( 2 ) INFORMATION FOR SEQ ID NO:20:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

GGGCCCGGGG GCCCTTTTGC TAATCATGTT CATACCTCTT 40

ATCTTCCTCC CACAGGCTGC GCGTTCTCGC 70

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

GGGCCCGGGT CAGTTAGCCT CCCCCAT 27